（12）United States Patent
Cotner

(10) Patent No.: US 8,145,353 B1
(45) Date of Patent: Mar. 27, 2012

(54) AUTOMATED RETRIEVAL AND DELIVERY OF MEDICATIONS

(76) Inventor: Dennis Cotner, Oklahoma City, OK (US)

( * ) Notice: Subject to any disclaimer, the term of this patent is extended or adjusted under 35 U.S.C. 154(b) by 505 days.

(21) Appl. No.: 12/390,994

(22) Filed: Feb. 23, 2009

Related U.S. Application Data

(60) Provisional application No. 61/066,524, filed on Feb. 21, 2008.

(51) Int. Cl.
*G06F 17/00* (2006.01)
(52) U.S. Cl. ......... 700/241; 700/236; 700/242; 700/244
(58) Field of Classification Search ................. 700/231, 700/242, 244, 241, 236; 221/30, 31
See application file for complete search history.

(56) References Cited

U.S. PATENT DOCUMENTS

| | | | |
|---|---|---|---|
| 4,518,208 A | | 5/1985 | Marder |
| 5,047,948 A | | 9/1991 | Turner |
| 5,368,187 A | * | 11/1994 | Poncetta et al. ............... 221/30 |
| 5,469,110 A | * | 11/1995 | Liao ............................... 327/536 |
| 5,502,944 A | | 4/1996 | Kraft et al. |
| 5,863,697 A | * | 1/1999 | Uchiyama et al. ....... 430/137.17 |
| 6,011,999 A | | 1/2000 | Holmes |
| 6,175,779 B1 | | 1/2001 | Barrett |
| 6,176,392 B1 | | 1/2001 | William et al. |
| 6,318,051 B1 | * | 11/2001 | Preiss .............................. 53/493 |
| 6,581,356 B2 | | 6/2003 | Kim |
| 6,985,870 B2 | | 1/2006 | Martucci et al. |
| 7,006,893 B2 | | 2/2006 | Hart et al. |
| 7,014,063 B2 | | 3/2006 | Shows et al. |
| 7,970,490 B2 | * | 6/2011 | Fellows et al. ................ 700/235 |

FOREIGN PATENT DOCUMENTS

| | | |
|---|---|---|
| GB | 0127443.0 | 11/2001 |
| GB | 0309000.8 | 4/2003 |
| GB | 0311143.2 | 5/2003 |
| WO | WO 02/098760 A1 | 12/2002 |

OTHER PUBLICATIONS

Paolo Fiorini and Chris Nugent, "A Robotic Aid for Medical Compliance at Home", pp. 1-17, Department of Informatics, University of Verona, Italy, School of Information and Software Engineering, University of Ulster at Jordanstown, UK.
Colleges of Nurses of Ontario, "Medication", 2005, pp. 1-28, Ontario, Canada.
Margaret Pugh, "State of Alaska Department of Corrections Policies and Procedures" "Medical and Health Care Services" "Use of Pharmaceutical Products", 2001, pp. 1-12, Alaska, US.

\* cited by examiner

*Primary Examiner* — Timothy Waggoner
(74) *Attorney, Agent, or Firm* — McAfee & Taft

(57) ABSTRACT

This invention relates to a process and a device for automatically delivering and retrieving singular medication from a plurality of containers or product blister packages, storing and recording medication transactions for each patient, and the crushing of designated medications. This invention also relates to medication control, delivery, consumption verification and monitoring within institutional entities.

37 Claims, 16 Drawing Sheets

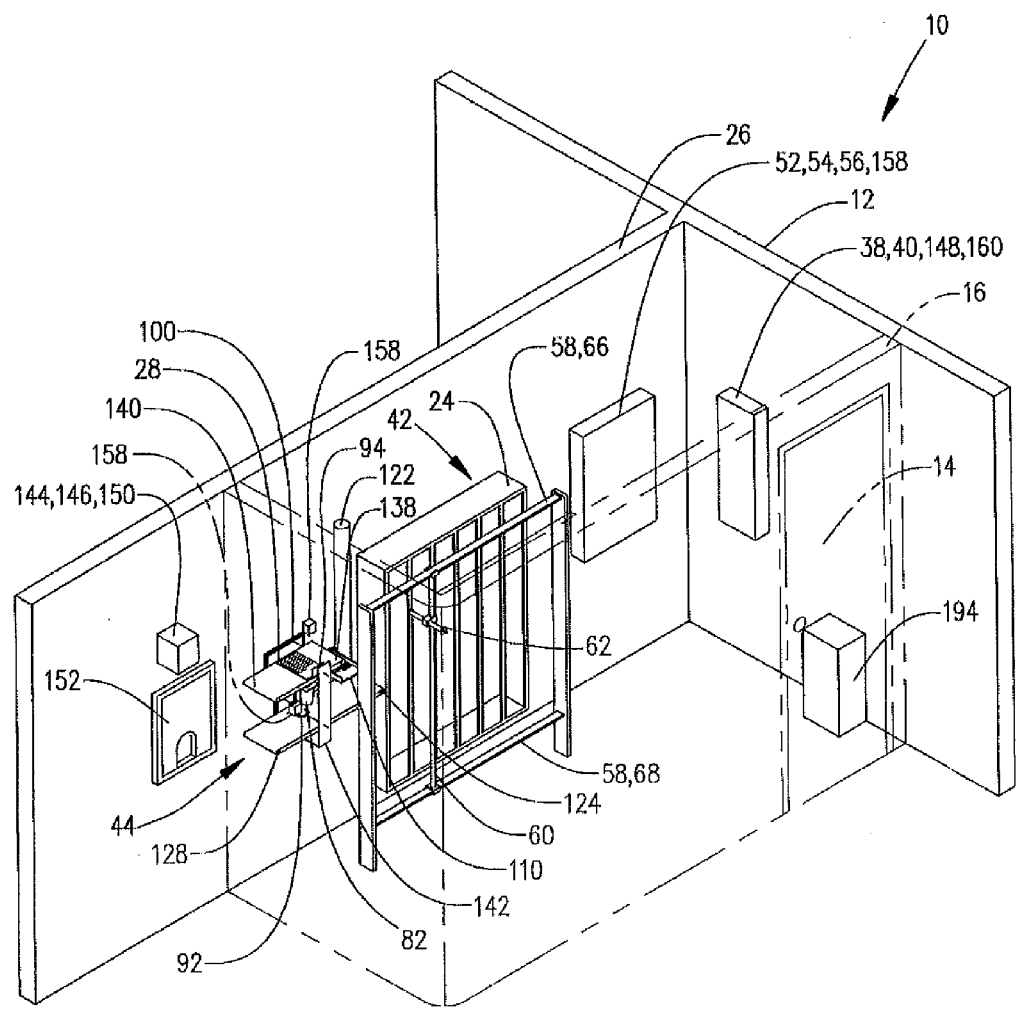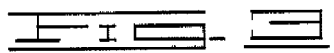

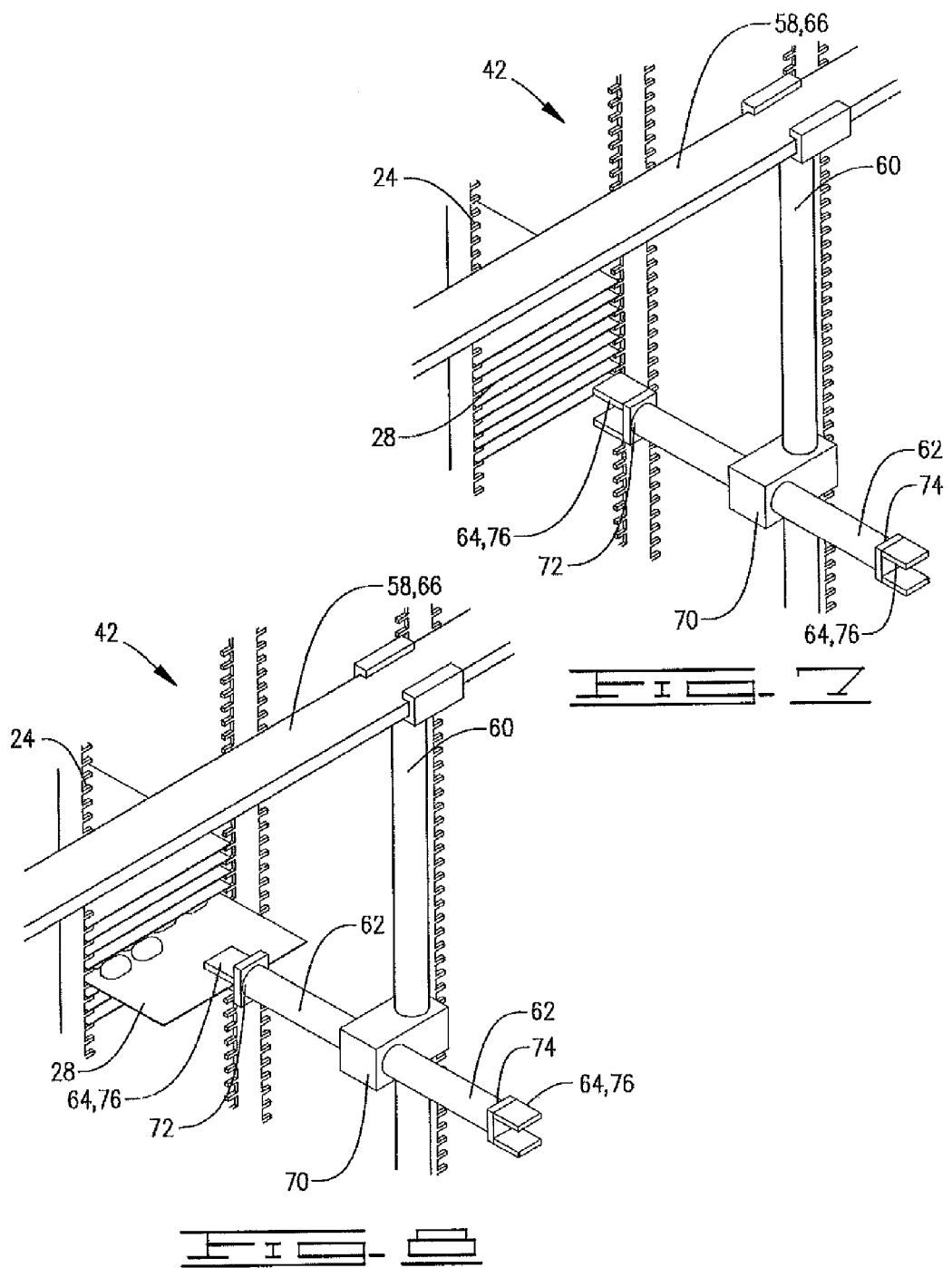

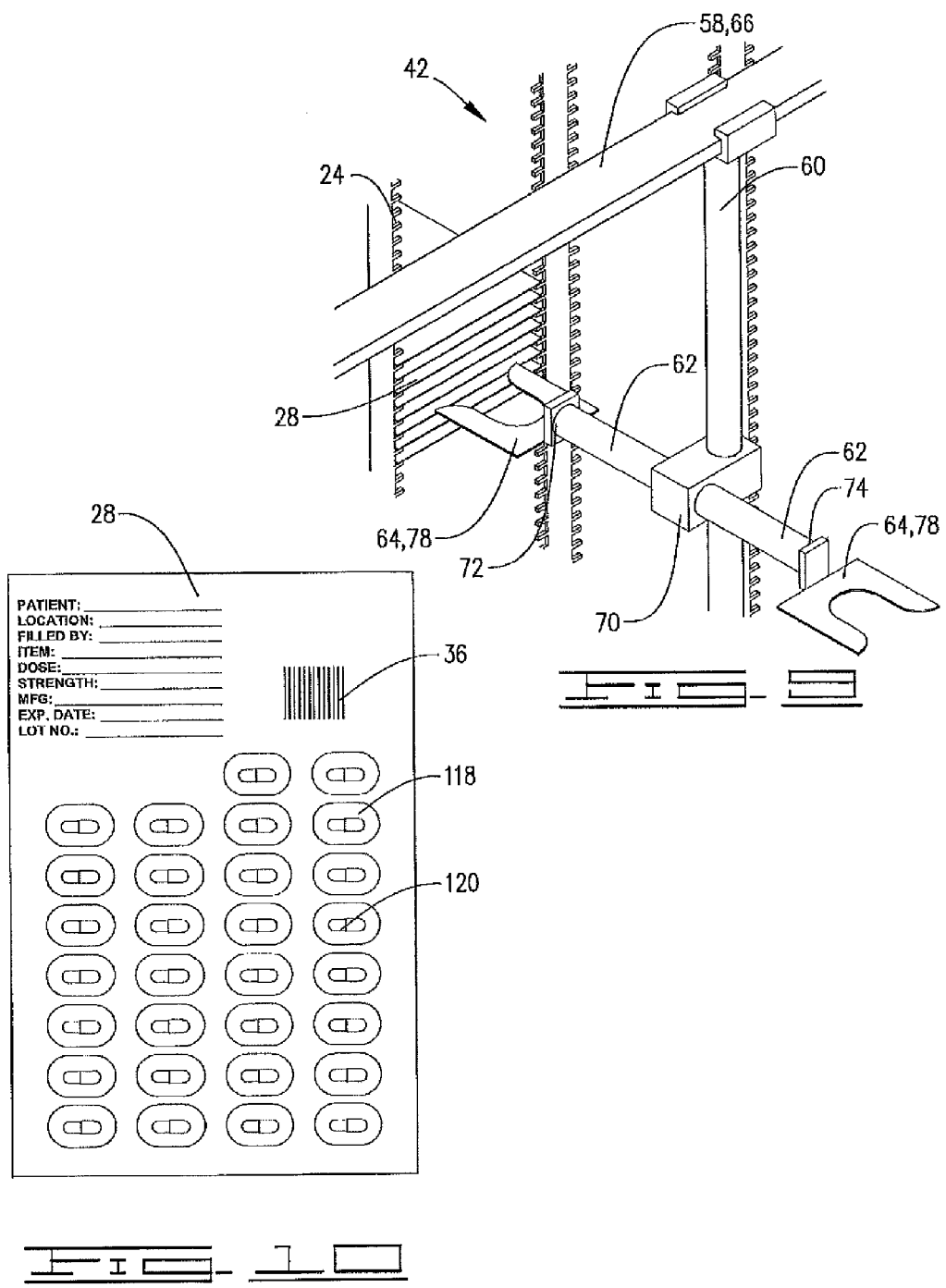

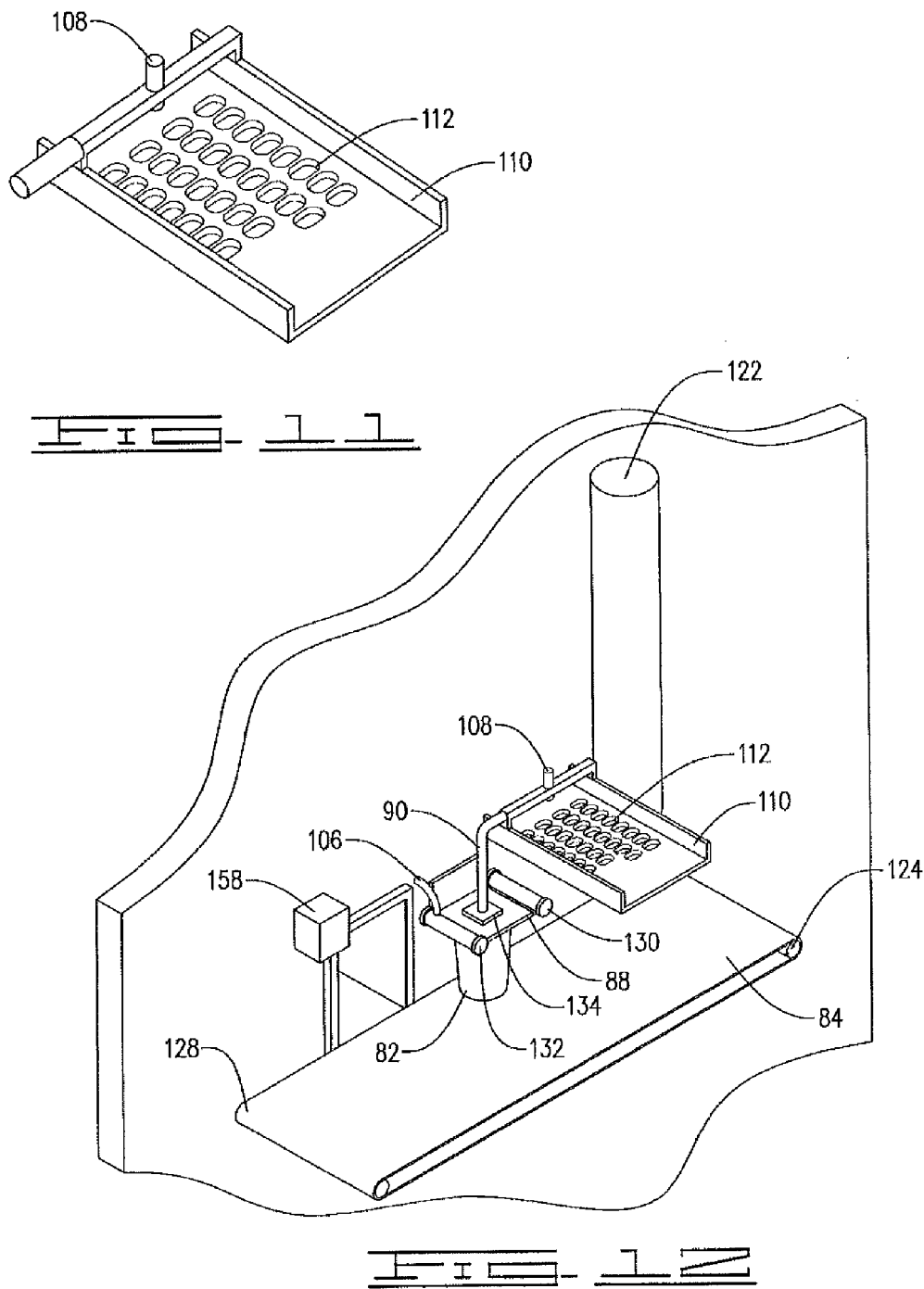

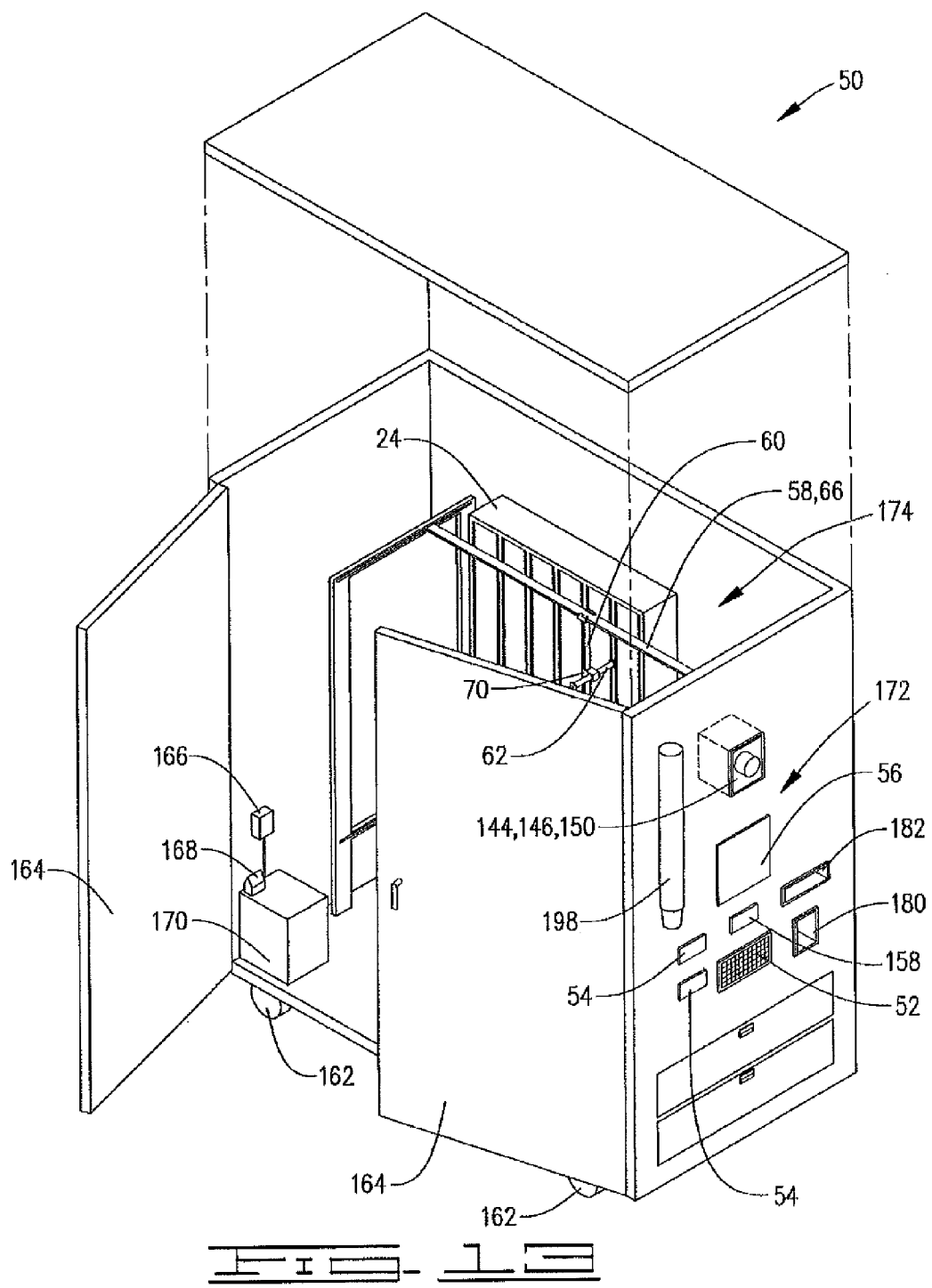

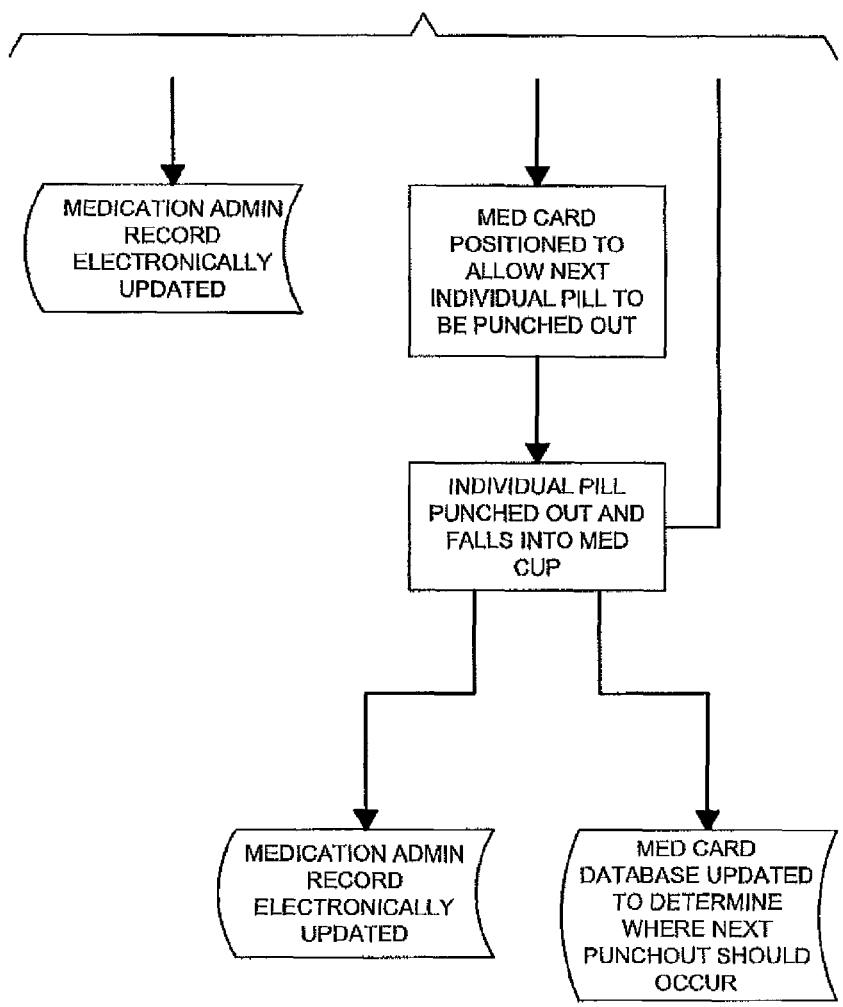
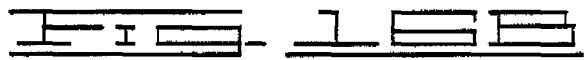

AUTOMATED RETRIEVAL AND DELIVERY OF MEDICATIONS

CROSS-REFERENCE TO RELATED APPLICATION

This application claims the benefit of U.S. Provisional application No. 61/066,524, filed Feb. 21, 2008.

BACKGROUND OF THE INVENTION

This invention relates to a process and a device for automatically retrieving singular medication from a plurality of containers or packaged product packs, storing and recording medication transactions for each patient, and the crushing of designated medications. This invention also relates to medication control, dispensing/delivery, consumption verification and monitoring within institutional entities.

Institutional entities such as correctional systems, nursing homes, assisted living centers and hospitals require the accurate administration of medications to a plurality of patients. This process can be time intensive with numerous opportunities for human error. The documentation of medication administration is often done manually, and is a tedious, inaccurate process that can be difficult to monitor. Maintaining an accurate inventory of medications, physical security, and accountability of controlled medications often requires additional personnel. Additionally, the linking of the delivery process and the billing process for medication is often inconsistent, and can be further complicated by inaccurate documentation and/or human error.

Another problem arises in the institutional environment when medication is left with the patient. The potential exists for abuse and/or theft of patient retained medication and patient compliance with dosage instructions is difficult to oversee and track. And again, problems related to theft and patient compliance are further compounded by the same inaccuracies and human error previously mentioned.

Secure institutions must ensure the accurate distribution and consumption of single pills by their patients. However, the labor costs associated with tracking a single pill exceed the costs associated with tracking a blister package. Thus, the preferred approach for dispensing a single pill is a blister package. However, current systems do not provide a mechanical system suitable for selecting a single blister package of medication from the pharmacy or medication room, and subsequently dispensing a single dosage from the blister pack by mechanical means is lacking. Additionally, secure institutional environments typically lack an autonomous and/or biometric system for positive patient identification, patient medication receipt, and medication consumption verification. Still further, there is an absence of a real-time feedback loop for administrative personnel to monitor strict patient compliance with the medication protocol.

In some institutions, medical/pharmacy personnel encounter safety hazards during the deliver of medications to the patient. The problems can be worse in a prison environment where medication may become currency. In these situations, an automated medication facility and/or cart having the ability to deliver and dispense the correct medication to a single patient or a series of patients would be preferred. Such a capability in this environment requires both security and electronic controls. Additionally, verification of patient consumption with real-time feedback or notification will be important. Thus, security, consumption control, verification, feedback and communications are essential to ensure that medication dispersement is not circumvented for other purposes.

In an institutional environment, mass medication delivery will improve operating efficiency and reduce costs. However, identification of a particular patient and their specific dose(s) can present a challenge. In many instances, the patient is unaware of the possible drug interactions or the side affects of the particular medication they are taking. An autonomous system that positively identifies the patient, selects the right medication, delivers the medication, verifies positive patient consumption and provides real-time feedback with the administrative medical/pharmacy personnel is highly desired. Additionally, institutions will benefit from an autonomous system that can provide real-time drug information to an institutional patient in a hardcopy form simultaneously with dispensing of the medication.

Medication inventory control for institutional entities is another distinct challenge. With a large number of medications ordered and dispensed daily, it is preferred to have a real-time medication inventory tracking and re-supply linked with the medication dispensing/delivery function. It is also highly desirable to have the ability to automatically track inventory on-hand, inventory re-supplying/reordering, pharmacy/medication room delivery, patient delivery, patient information sheets, and drug interaction sheets. Because of the large number of personnel involved in the medication delivery process, there are additional concerns about the accountability, security, and tracking of medication. Often, there is a breakdown and/or a complete lack of medication security and tracking.

The present invention, as described herein, solves the aforementioned problems and deficiencies.

SUMMARY OF THE INVENTION

In a one embodiment, the current invention provides an automated medication delivery system comprising a storage facility, a controller, at least one input station, a retrieval device, a cup, a cup slot, and a med card slot.

The storage facility has a plurality of storage bins. The storage bins are sized for storing a med card.

The controller is in electronic communication with a computer. The controller is attached to the storage facility and adapted to provide control of the storage facility.

At least one input station incorporated with the storage facility and in electronic communication with the controller is provided. The input station includes an input port, a positive identification device, and a display device. The input port is positioned on a side of the storage facility for entering a user's personal identification data. The display device provides a menu depicting at least one medication associated with a patient and currently available for dispensing.

The retrieval device is positioned inside of the storage facility and is capable of retrieving the med cards from the storage bins.

The punchout system is positioned inside of the storage facility and is adapted to receive the med cards from the retrieval device. The punchout system includes a punch and a tray. The tray is sized to hold the med card and has a plurality of holes thereon. The holes are compatible with a plurality of pills positioned on the med card.

The cup is positioned on a conveyor that is positioned inside of the storage facility. The cup is positioned below the hole of the punch out and is adapted to receive one of a plurality of the pills from the med card.

The cup slot is positioned in the side of the storage facility. The cup slot is adapted to receive the cup. The med card slot is positioned in the side of the storage facility. The med card slot is adapted to dispense the med card.

In another embodiment, an automated medication delivery system is provided. The automated medication delivery system comprises: a facility, a controller, a barcode scanner, an input station, a retrieval device, a dispensing device, and a positive consumption device.

The facility includes a secure interior and a plurality of storage bins positioned within the secure interior. The storage bins are sized to store a med card.

The controller is in electronic communication with a computer. The controller is attached to the facility and is adapted to control the facility. The controller stores information associated with each of the med cards.

The barcode scanner is positioned within the facility and is capable of scanning the med cards before insertion into the storage bins and after removal from the storage bins. The barcode scanner is in electronic communication with the controller.

At least one input station incorporated with the storage facility and in electronic communication with the controller is provided. The input station includes an input port, a positive identification device, and a display device. The input port is positioned on a side of the storage facility for entering a user's personal identification data. The display device displays a menu of at least one medication associated with a patient and that is available for dispensing.

The retrieval device is in electronic communication with the controller and is positioned within the facility. The retrieval device includes: a track, an elevation rod, a picker arm, and a retriever. The elevation rod is movably mounted in the track. The picker arm is moveably mounted on the elevation rod. The retriever is attached to the picker aim.

The dispensing device is positioned within the facility. The dispensing device includes: a punchout system, a cup, a first conveyor, a second conveyor, an anti-contamination film, a pill crusher, a cup sweeper, a med card sweeper, at least one cup dispensing slot, and at least one med card dispensing slot. The punch out is positioned inside of the facility and is in electronic communication with the controller. The punchout system is adapted to receive the med card from the retrieval device. The punchout system includes a punch and a tray. The tray is sized to hold the med card. The tray has a plurality of holes thereon. The holes are compatible with a plurality of pills positioned on the med card. The cup is positioned below the holes and is sized to receive one of the plurality of pills. The first conveyor has the cup positioned thereon. The second conveyor is positioned to receive the med card. The anti-contamination film is mounted on and stretched between a first and a second spool. The pill crusher has a crusher head and is positioned between the first and second spools. The anti-contamination film is positioned between the crusher head and an interior of the cup. The cup sweeper is positioned to move the cup from the first conveyor. The med card sweeper is positioned to move the med card from said second conveyor. The cup dispensing slot is positioned to receive the cup from the cup sweeper. The med card dispensing slot is positioned to receive the med card from the med card sweeper.

The positive consumption feedback device is in electronic communication with the controller. The positive consumption feedback device includes a video camera, a microphone, a recorder, and an audio/video communications link. The video camera is positioned on the side of the facility. The recorder is capable of recording video from the video camera and audio from the microphone. The audio/video communications link is with a separate location. The audio/video communications link provides real-time video and audio to the separate location.

In yet another embodiment, the current invention provides a mobile automated medication delivery system comprising: a cart, a plurality of storage bins, a controller, a wireless communications device, at least one input station, a retrieval device, a punchout system, a cup, a cup slot, and a med card slot.

The cart has a plurality of storage bins internally positioned within it. At least one med card carrying a plurality of medications positioned within at least one storage bin is provided.

The controller is in electronic communication with a computer and attached to the cart. The controller is adapted to provide control of the cart.

The wireless communications device provides electronic communication for the controller. The controller is in electronic communication with a remote central control facility.

The input station is incorporated with the cart and is in electronic communication with the controller. The input station includes an input port, a positive identification device, and a display device. The input port is positioned on a side of the cart and is for entering a user's personal identification data. The display device displays a menu of at least one medication associated with a patient and is available for dispensing.

The retrieval device is positioned inside of the cart and is capable of retrieving the med cards from the storage bins.

The punchout system is positioned inside of the cart and is adapted to receive the med card from the retrieval device. The punchout system includes a punch device and a tray. The tray is sized to hold the med card. The tray has a plurality of holes thereon that are compatible with a plurality of pills positioned on the med card.

The cup is positioned on a conveyor that is positioned inside of the cart. The cup is positioned below the holes of the punch out and is adapted to receive a pill from the med card.

The cup slot is positioned in the side of the cart. The cup slot is adapted to dispense the cup. The med card slot is positioned in the side of said cart. The med card slot is adapted to dispense the med card.

In yet another embodiment, a method for dispensing medication in a secure facility is provided. The method comprises the steps of:

(a) a requestor logging on to an automated medication delivery system;
(b) identifying said requestor through a security protocol, said security protocol including:
   i. said requestor entering a unique identifier associated with said requestor;
   ii. said requestor entering a security password/personal identification number;
   iii. comparing said entries by said requestor with a database in a controller electronically connected to and communicating with said automated medication delivery system;
(c) displaying at least one medication available for a patient from a list of available medications for said patient, said list of available medications stored in a patient database;
(d) selecting at least one medication from said list;
(e) directing said controller to retrieve said medication from a storage bin located in said automated medication delivery system;
(f) scanning said selected medication with a barcode reader;
(g) verifying said scanned medication matches said selected medication;
(h) dispensing said medication according to a pre-selected protocol;

(i) printing a receipt for said patient, said receipt having information regarding said medication; and j) updating said patient database.

Numerous objects and advantages of the invention will become apparent as the following detailed description of the preferred embodiments is read in conjunction with the drawings which illustrate such embodiments.

DRAWINGS

FIG. 3 is a back perspective view of the automated medication delivery system with the walls removed.

FIG. 7 is a perspective view of the retrieval device.

FIG. 8 is a perspective view of the retrieval device extracting a med card using a clamp.

FIG. 9 is a perspective view of the retrieval device extracting a med card using a spatula.

FIG. 10 is a top view of a med card.

FIG. 11 is a perspective view of a tray.

FIG. 12 is an elevation view of a punchout system.

FIG. 13 is a front perspective view of the mobile automated medication delivery system.

FIGS. 16A and 16B depict the flow chart of a staff member login and retrieval of a patient's medication.

DETAILED DESCRIPTION

As described herein, the preferred embodiments of the current invention provide a method and apparatus related to automatically storing and delivering medications within an institutional facility. The method and apparatus maintains the security of the medication and ensures patient compliance with the medicine protocol.

Figure 1:
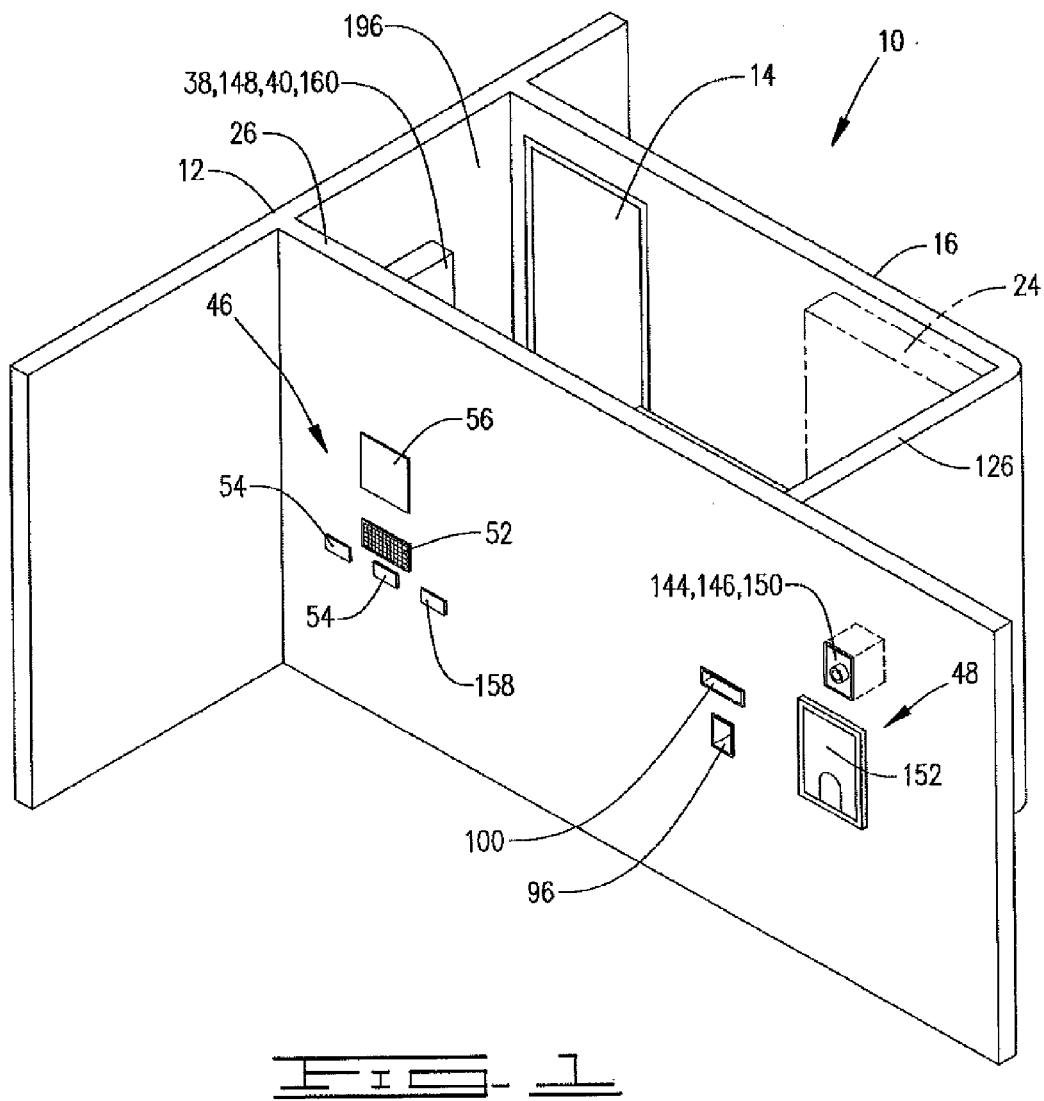
FIG. 1 is a front perspective view of the automated medication delivery system.
Figure 2:
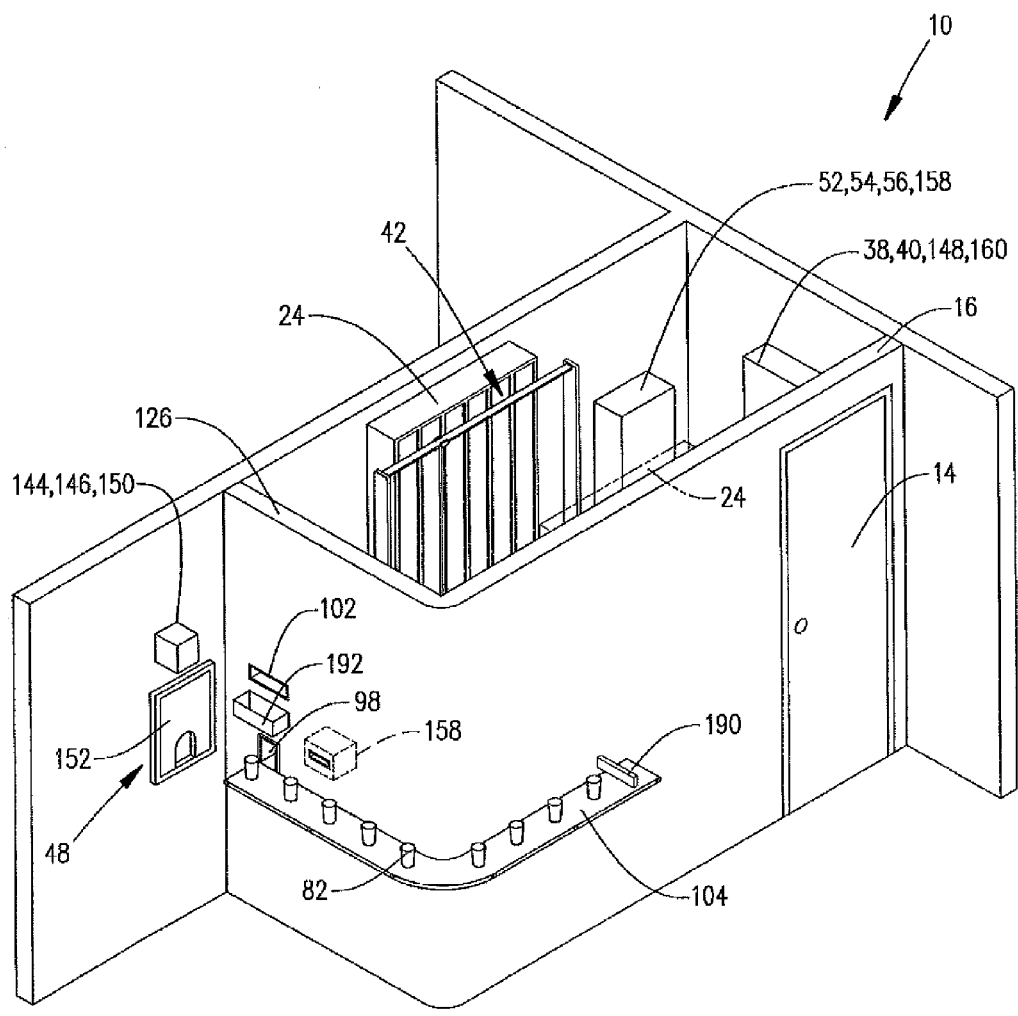
FIG. 2 is a back perspective view of the automated medication delivery system.

Referring to the drawings and specifically to FIGS. 1-14, the automated medication delivery system is illustrated and generally designated by the numeral 10. FIG. 1 represents a front perspective view of automated medication delivery system 10.

Referring to FIGS. 1-5, automated medication delivery system 10 includes a storage facility 12. Storage facility 12 is a secure area having a single access door 14. Access door 14 is positioned within inner side wall 16 of storage facility 12 providing access to storage bins 24. Preferably, a plurality of storage bins 24 are positioned along inner side wall 16 and outer side wall 26, aligned in at least two rows.

Figure 5:
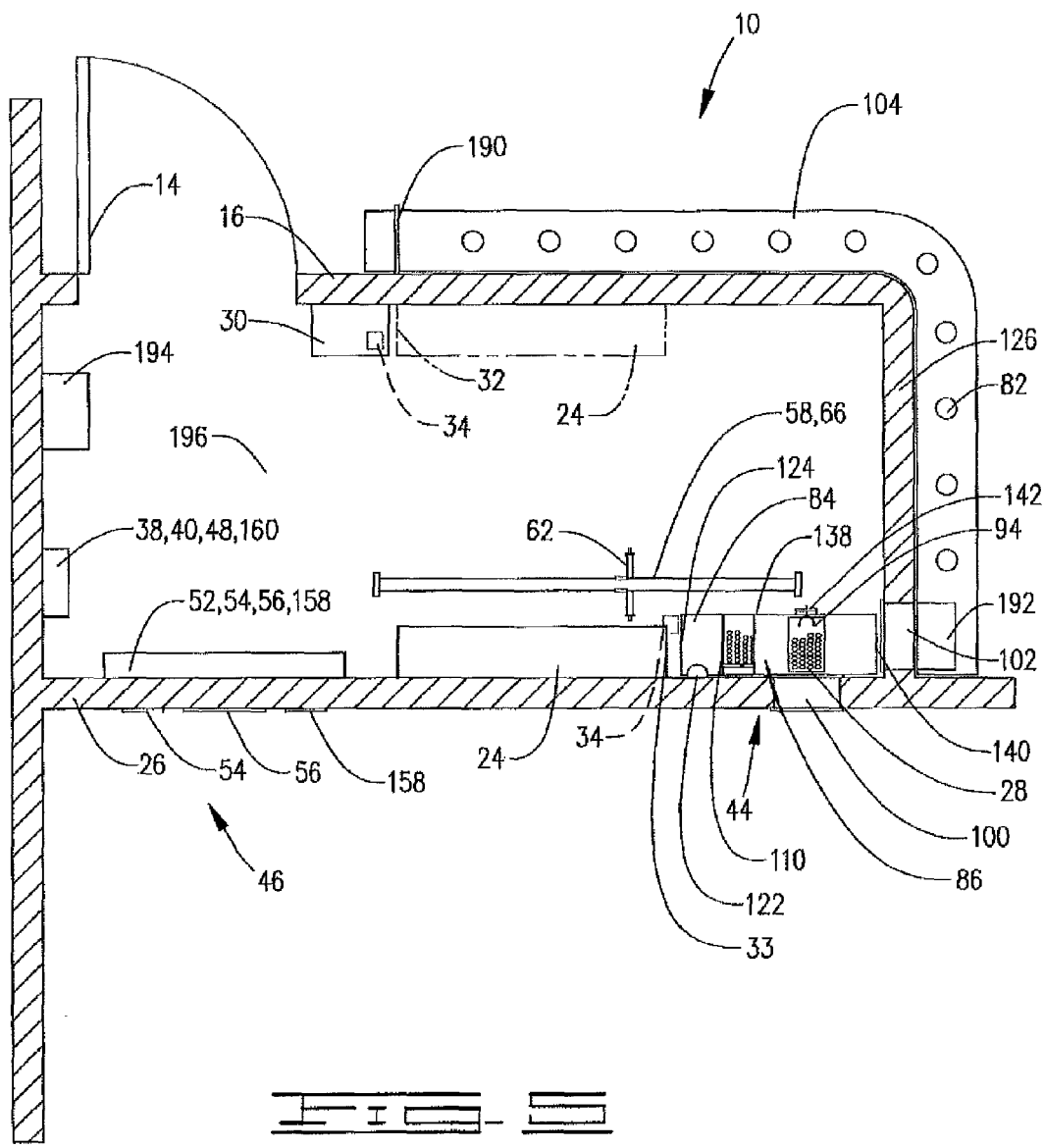
FIG. 5 is a top view of the automated medication delivery system.
Figure 6:
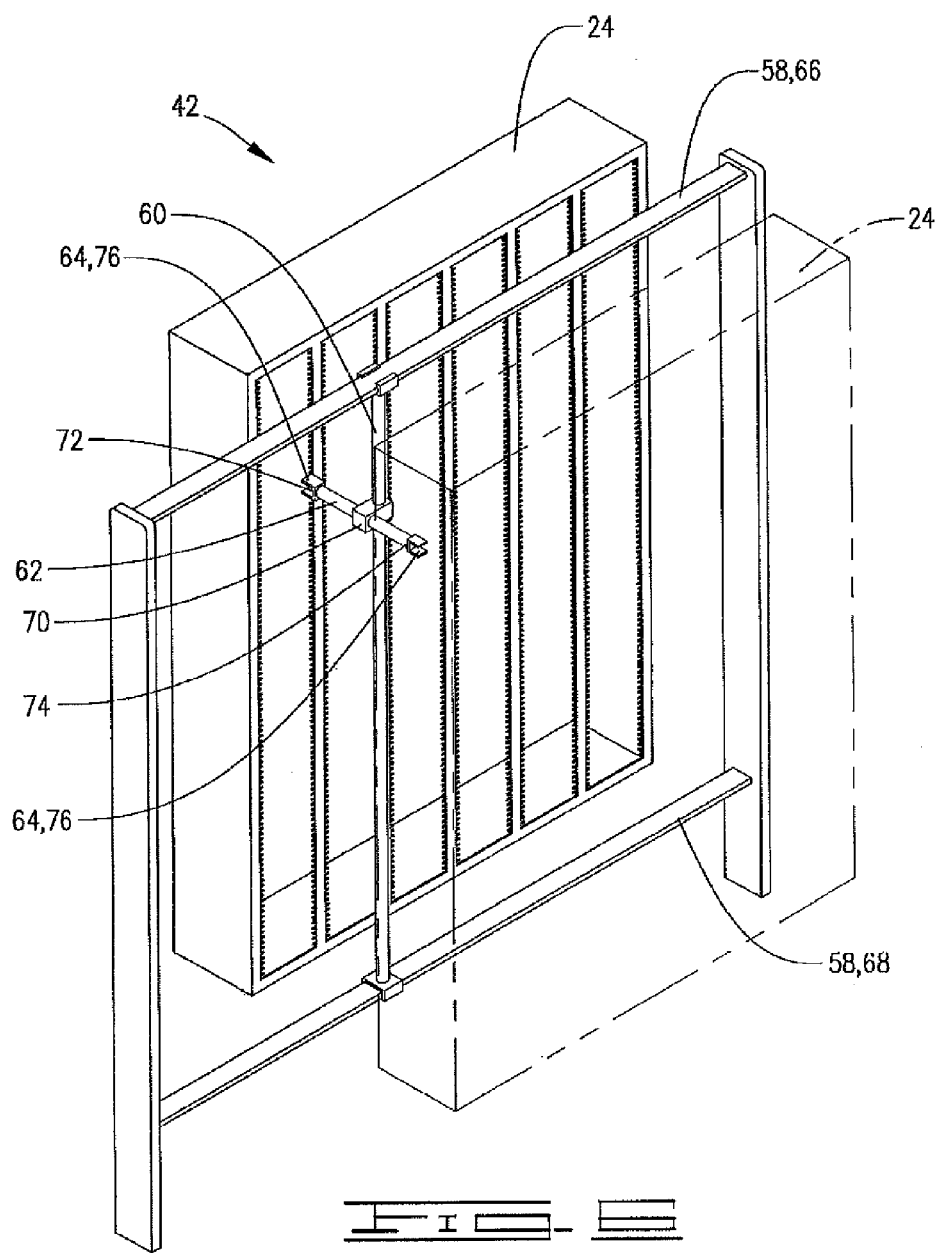
FIG. 6 is a back perspective view of the storage bins and retrieval device.

Each of storage bins 24 are sized to accept med card 28, shown in FIG. 10 and described herein. Preferably, storage bins 24 are vertically and laterally aligned to form a plurality of storage bins 24. As shown in FIG. 5, access panel tray 30 is positioned next to bin end 32 of storage bins 24.

Automated medication delivery system 10 also includes a barcode scanner 34. Barcode scanner 34 is positioned near access panel tray 30 or near bin end 33. Preferably, barcode scanner 34 is positioned to provide a sufficient field of view to read barcode 36 of med card 28. It may be desirable to have at least two barcode scanners 34, with one positioned in each location.

Controller 38 is positioned within storage facility 12 as shown in FIG. 5. Controller 38 may be positioned in any location as long as it is electronically connectable to numerous components of automated medication delivery system 10 as identified herein. Controller 38 is in electronic communication with a computer 40. Controller 38 provides functional control for all of automated medication delivery system 10. For example, controller 38 receives input, provides output and real-time feedback to all systems. Some of the major systems include barcode scanner 34, retrieval device 42, dispensing device 44, first input station 46, positive control feedback device 48, and cart 50.

Computer 40 is preferably incorporated into controller 38. However, for security reasons computer 40 may be separated from controller 38.

With reference to FIGS. 1 and 5, first input station 46 includes input port 52, at least one positive identification device 54, and display device 56. In the preferred embodiment, input port 52 is a keyboard, as shown in FIG. 1; however, input port 52 maybe any device suitable for entering personal identification data into controller 38. Positive identification device 54 is preferably a biometric device such as finger print reader, retinal scanner, or voice identification device. Display device 56 is a visual display interacting with the requestor. Preferably, display device 56 is a touchscreen device. In one alternative, when display device 56 is a touch screen display device, input port 52 is integrated with display device 56. First input station 46 elements, input port 52, positive identification device 54, and display device 56, are in electronic communication with controller 38.

Additionally, first input station 46, input port 52 and display device 56 may be used to submit live queries or respond to medical/pharmacy personnel or security personnel.

Retrieval device 42 is preferably positioned between storage bins 24 and in electronic communication with controller 38. As shown in FIGS. 3-9, retrieval device 42 includes track 58, elevation rod 60, picker arm 62, and retriever 64. Track 58 permits lateral movement of elevation rod 60 between storage bins 24. Track 58 supports elevation rod 60 between upper component 66 and lower component 68

Elevation rod 60 carries a rotatable collar 70 supporting picker arm 62. Elevation rod 60 provides vertical movement of between storage bins 24 for picker arm 62, while rotatable collar 70 allows picker arm 62 to rotate 360 degrees about elevation rod 60. Picker arm 62 is able to laterally move within rotatable collar 70.

Each picker arm end 72 and 74 carries a retriever 64. In one preferred embodiment depicted in FIGS. 6-8, retriever 64 carries clamping device 76. In an alternative embodiment depicted in FIG. 9 retriever 64 carries spatula shaped device 78.

Dispensing device 44 is shown in FIGS. 3-5 and 11. Dispensing device 44 includes punchout system 80, cup 82, first conveyor 84, second conveyor 86, anti-contamination film 88, pill crusher 90, cup sweeper 92, med card sweeper 94, first cup dispensing slot 96, second cup dispensing slot 98, first med card dispensing slot 100, second med card dispensing slot 102, a distribution conveyor 104, and water dispenser 106.

Punchout system 80 includes punch 108 and tray 110, and is adapted to extract medication from med card 28. A plurality of holes 112 are disposed through tray 110 and positioned above catch 114. Catch 114 has catch opening 116.

With reference to FIG. 10, med card 28 has blisters 118 containing pills 120. Positioning of med card 28 in tray 110 aligns blisters 118 with holes 112. Extraction of pills 120 is provided by positioning of punch 108 over any one of blisters 118.

Figure 4:
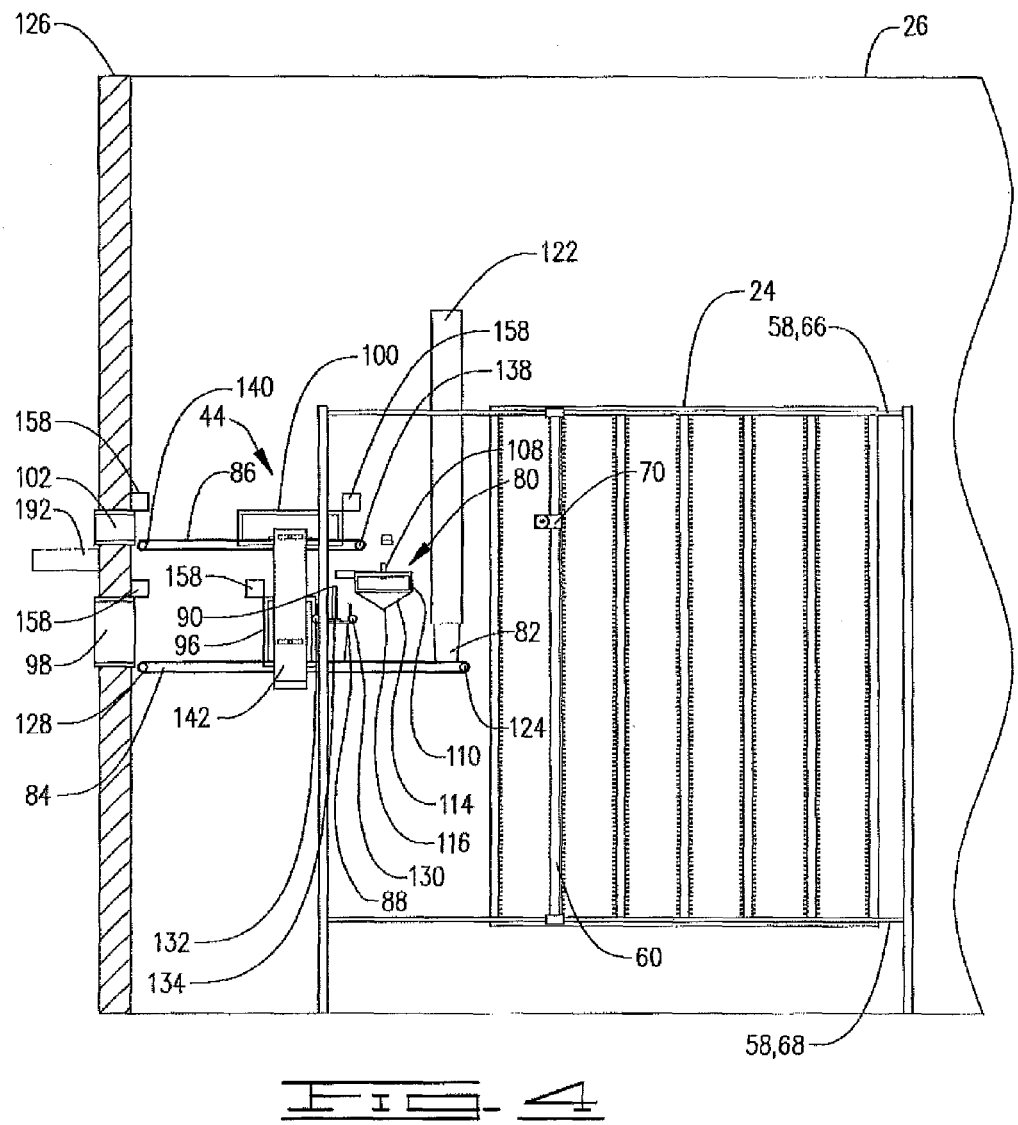
FIG. 4 is an elevation view of the automated medication delivery system.

With reference to FIGS. 3 and 4, cup feeder 122 is positioned at first conveyor first end 124. Cup feeder 122 provides a continuous supply of individual cups 82 to conveyor 84. First conveyor 84 is adapted to convey cup 82 to first cup dispensing slot 96 positioned through outer side wall 26 or second cup dispensing slot 98 positioned through first end wall 126 at first conveyor second end 128.

Anti-contamination film 88 is positioned between and crusher head 134 of pill crusher 90 and an interior of cup 82. Anti-contamination film 88 is carried by first spool 130 and second spool 132. First spool 130 and second spool 132 are adapted to release a portion of anti-contamination film 88 when crusher head 134 is positioned within the interior of cup 82, and to retract anti-contamination film 88 when crusher head 134 is not in use. First spool 130 and second spool 132 are adapted to move anti-contamination film 88 after every crushing event. Preferably, pill crusher 90 moves in an upward and downward direction for crushing pill 120. Pill crusher 90, first spool 130, and second spool 132 are in electronic communication with controller 38.

Second conveyor 86, shown in FIGS. 3-5, receives a complete med card 28. Second conveyor 86 has a second conveyor first end 138 adapted to receive med card 28 from retrieval device 42. Second conveyor 86 is adapted to convey med card 28 to first med card dispensing slot 100, or second med card dispensing slot 102. First med card dispensing slot 100 is positioned through outer side wall 26. Second med card dispensing slot 102 is shown positioned through first end wall 126 at second conveyor second end 140.

Sweep structure 142 supports cup sweeper 92 and med card sweeper 94. Cup sweeper 92 is positioned to move cup 82 from first conveyor 84 to first cup dispensing slot 96. Med card sweeper 94 is positioned to move med card 28 from second conveyor 86 to first med card dispensing slot 100.

When requested, first conveyor 84 conveys a plurality of cups 82 through second cup dispensing slot 98 to distribution conveyor 104. Distribution conveyor 104 is shown wrapping around first end wall 126 and onto inner side wall 16. Distribution conveyor 104 is positioned within a secure portion of storage facility 12.

Positive consumption feedback device 48 is shown in FIG. 1. Positive consumption feedback device 48 ensures compliance with medical protocols by providing a video camera 144, microphone 146, recorder 148 and audio/video communications link 150 to permit monitoring of patients using automated medication delivery system 10. Additionally, window 152 permits direct human oversight by facility staff standing in or outside of window 152. Although video camera 144, microphone 146, recorder 148 and audio/video communications link 150 can be positioned almost anywhere. In one embodiment, window 152 has video camera 144 and microphone 146 positioned above it. Audio/video communications link 150 provides a signal to recorder 148 co-located with controller 38.

Dispensing device 44 optionally includes a water dispenser 106. Water dispenser 106 is adapted to provide water to cup 82 while upon first conveyor 84, as seen in FIG. 12.

In the preferred embodiment, a printer 158 prepares a receipt for the medication. In one embodiment, printer 158 prepares a receipt near input port 52. The receipt optionally includes additional information regarding the medication dispensed. Another embodiment has an additional printer near first cup dispensing slot 96 for dispensing a receipt with cup 82. Preferably, another printer 158 is positioned to deposit a receipt with cup 82 exiting second cup dispensing slot 98. Additionally, a portable printer (not shown) may be near window 152 for a staff member to manually present to the patient.

As depicted in FIG. 10, med card 28 carries a barcode 36. Additional information is also preferably printed on med card 28. The preferred information includes identification of the medication, date of issue, number of refills, prescribing medical professional, dosage, administration protocol, warnings, and housing unit, or room of the patient. Other information can be added as desired. Preferably, database 160 stores all information for access by computer 40 through controller 38.

Servicing of retrieval device 42, dispensing device 44, barcode scanner 34, controller 38, first input station 46, or any other equipment with medication room 196 is done by qualified personnel. This includes refilling cup feeder 122, picking up dropped med cards 28, or cleaning spills.

Figure 14:
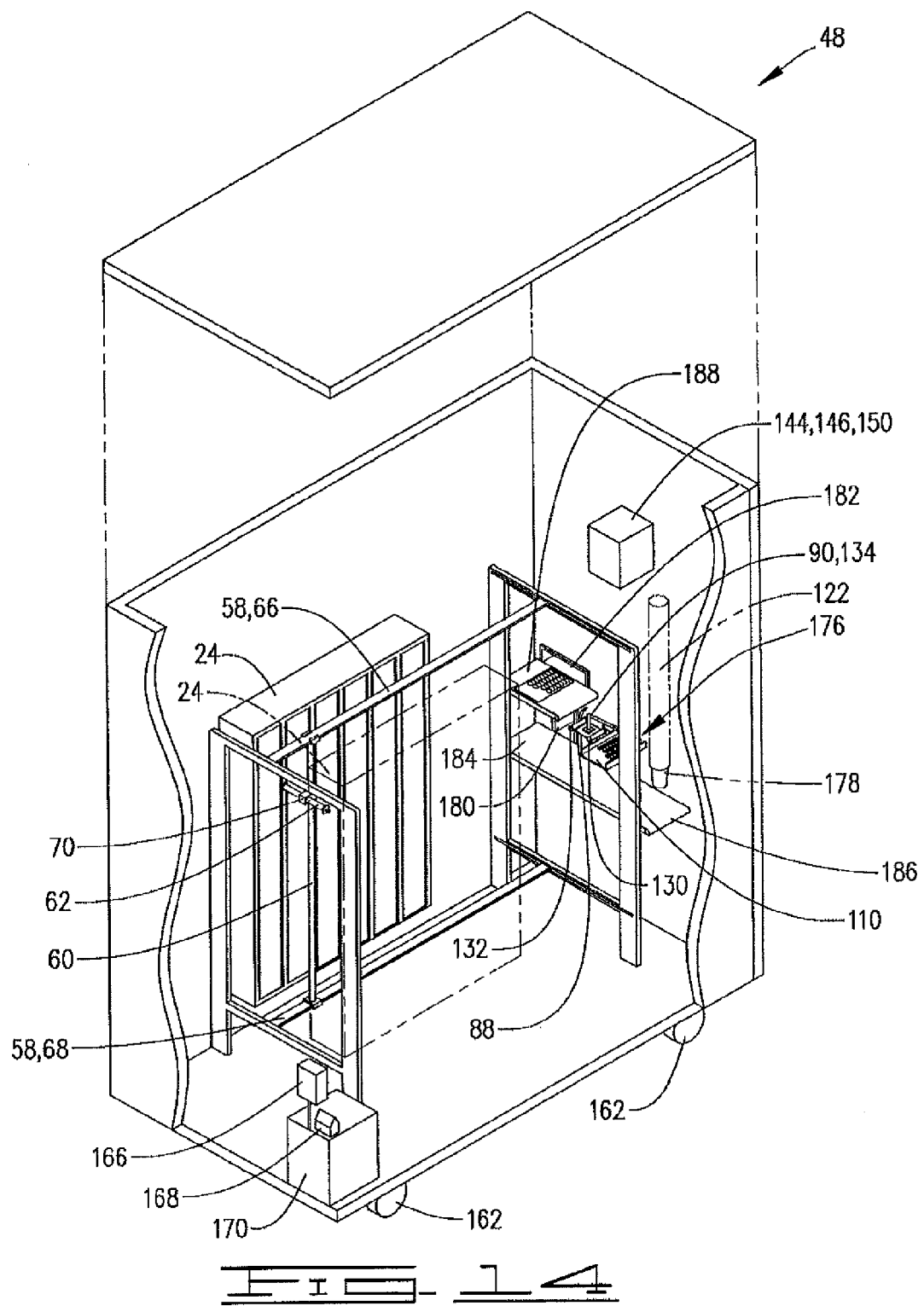
FIG. 14 is a back perspective view of the interior of the mobile automated medication delivery system.

In the preferred embodiment, cart 50 is a mobile extension of automated medication delivery system 10. FIGS. 13 and 14 show cart 50 carried by wheels 162. However, cart 50 may use any convenient type of conveyance suitable for movement through the intended environment. Additionally, cart 50 may have powered wheels 162 for autonomous operations or robotic operations.

Cart 50 preferably uses a rechargeable battery as a power source (not shown) and includes a suitable charger (not shown) connectable to a standard wall outlet.

Cart 50 has a plurality of internal storage bins 24 sized to store med card 28. In the preferred embodiment, security is provided by access panels 164 that are only openable by the facility staff members with the proper access clearance.

Cart 50 further includes a wireless communication system suitable for communicating with controller 38. When operating in an autonomous mode or robotic mode, cart 50 is entirely controlled by controller 38. In this situation, controller 38 is a remote central control facility. A typical wireless communication system will include an antenna 166 and communications device 168 positioned within or on cart 50. Additionally, cart 50 has an on-board computer 170 for local control functions.

In the preferred embodiment, cart 50 has a remote input station 172, a remote retrieval device 174, a remote punchout 176, a cup 178, a remote cup dispensing slot 180, and a remote med card slot 182. Each of these is similar to the ones found in storage facility 12.

Additionally, remote input station 172 includes the same elements as found in input station 46. Remote input station 172 has input port 52, positive identification device 54, and display device 56. On remote input station 172, input port 52 is shown as a keyboard in FIG. 13. As before, input port 52 is suitable for entering personal identification data into cart 50 and controller 38. Display device 56 is a visual display interacting with the requestor. Preferably, display device 56 is a touchscreen device. In one alternative, when display device 56 is a touch screen display device, input port 52 is integrated with display device 56. Remote input station 172 is in electronic communication with on-board computer 170 and in wireless electronic communication with controller 38.

Remote retrieval device 174 also includes the same elements found in retrieval device 42. Remote retrieval device 174 is shown in FIGS. 13 and 14 as being positioned near and providing access to storage bin 24. Remote retrieval device 174 is in electronic communication with on-board computer 170 and in wireless electronic communication with controller 38.

FIGS. 13 and 14 show remote retrieval device 174 with track 58, elevation rod 60, picker arm 62, and retriever 64. Elevation rod 60 is movably positioned on track 58. Within cart 50, track 58 is shown with an upper component 66 and a lower component 68. Track 58 is designed to move elevation rod 60 laterally between storage bins 24.

Cart 50 uses picker arm 62, which is shown positioned on elevation rod 60. Elevation rod 60 is designed to move picker arm 62 vertically between storage bins 24. Picker arm 62 is mounted on rotatable collar 70. Rotatable collar 70 allows picker arm 62 to rotate 360 degrees about elevation rod 60. Picker arm 62 is able to laterally move within rotatable collar 70. Picker arm 62 in cart 50 also employs either clamping device 76 or spatula shaped device 78 as retriever 64. Within cart 50, retriever 64 is attached to at least end 72. Preferably, retriever 64 is attached to both ends 72 and 74 of picker arm 62.

Cart 50 employs a variation of dispensing device 44. As shown in FIG. 14, cart 50 uses punchout system 80, which includes punch 108 (not shown in FIG. 14) and tray 110. Tray 110 has a plurality of holes 110 disposed through it with catch 114 positioned below tray holes 112 of tray 110. Catch 114 has catch opening 116.

Cart conveyor 184 is adapted to convey a pill 120 extracted by punchout system 80 to remote cup dispensing slot 180. Remote cup dispensing slot 180 is shown positioned through outer side wall 26. Remote cup dispensing slot 180 is sufficiently large enough to allow access to pill 120 on cart conveyor 184.

Although not shown in FIG. 14, cart 50, an alternative embodiment includes a pill crusher 90. In this alternative embodiment, pill crusher 90, first spool 130, second spool 132, crusher head and anti-contamination film 88 are similarly configured as in storage facility 12. In cart 50, pill crusher 90, first spool 130, second spool 132, crusher head and anti-contamination film 88 are positioned between tray 110 and cart cup dispensing slot 180. Pill crusher 90, first spool 130 and second spool 132 are in electronic communication with on-board computer and in wireless electronic communication with controller 38.

In the alternative embodiment using pill crusher 90, cup feeder 122 is also used. In this alternative embodiment, cart conveyor 184 receives cups from cup feeder 122 which is positioned at cart conveyor first end 186. Cup feeder 122 provides a continuous supply of individual cups 82 to cart conveyor 184. Cart conveyor 84 conveys pill 120 positioned within cup 82 to remote cup dispensing slot 180. Remote cup dispensing slot 180 is also sufficiently large enough to allow access to cup 82 on cart conveyor 184.

As shown in FIG. 14, cart 50 uses cart shelf 188 to receive a complete med card 28. Cart shelf 188 is positioned adjacent to remote med card slot 182. Remote retrieval device 174 positions med card 28 sufficiently within remote med card slot 182 for a requestor to extract med card 28.

An alternative positive consumption feedback device 48 including video camera 144, microphone 146, recorder 148 and audio/video communications link 150 is optionally integrated with cart 50. Video camera 144, microphone 146, recorder 148 and audio/video communications link 150 are positioned near remote input station 172 for ease of use. Audio/video communications link 150 provides a signal to on-board computer 170 and wirelessly communicates with recorder 148 via controller 38.

In one alternative embodiment, cart 50 includes printer 158. Typically, printer 158 will be located near remote input station 172 for ease of use.

Having described the preferred embodiments of the apparatus of the current invention, the following discussion will focus on the preferred methods for automatically delivering medication using the automated medication delivery system 10. The following detailed discussion will break the method into six sub-methods, as shown in FIGS. 15-18. The first sub-method begins with the actual prescription process. The method includes the following steps, which are shown in FIG. 18:

a. A physician writes a prescription for medication(s) for a patient;
b. the prescription is transmitted to a pharmacy via computer or facsimile;
c. the pharmacy fills the prescription into med cards 28 having blisters 118;
d. the pharmacy records patient information and medicine information into database 160, and associates that information with barcode 36 that is printed on med card 28;
e. the patient information and prescription information are printed onto med card 28;
f. the pharmacy ships med cards 28 to facility via approved, overnight shipping agent; and
g. the staff receives, inspects, records anomalies and loads medicine cards loaded into automated medication delivery system 10.

Figure 17:
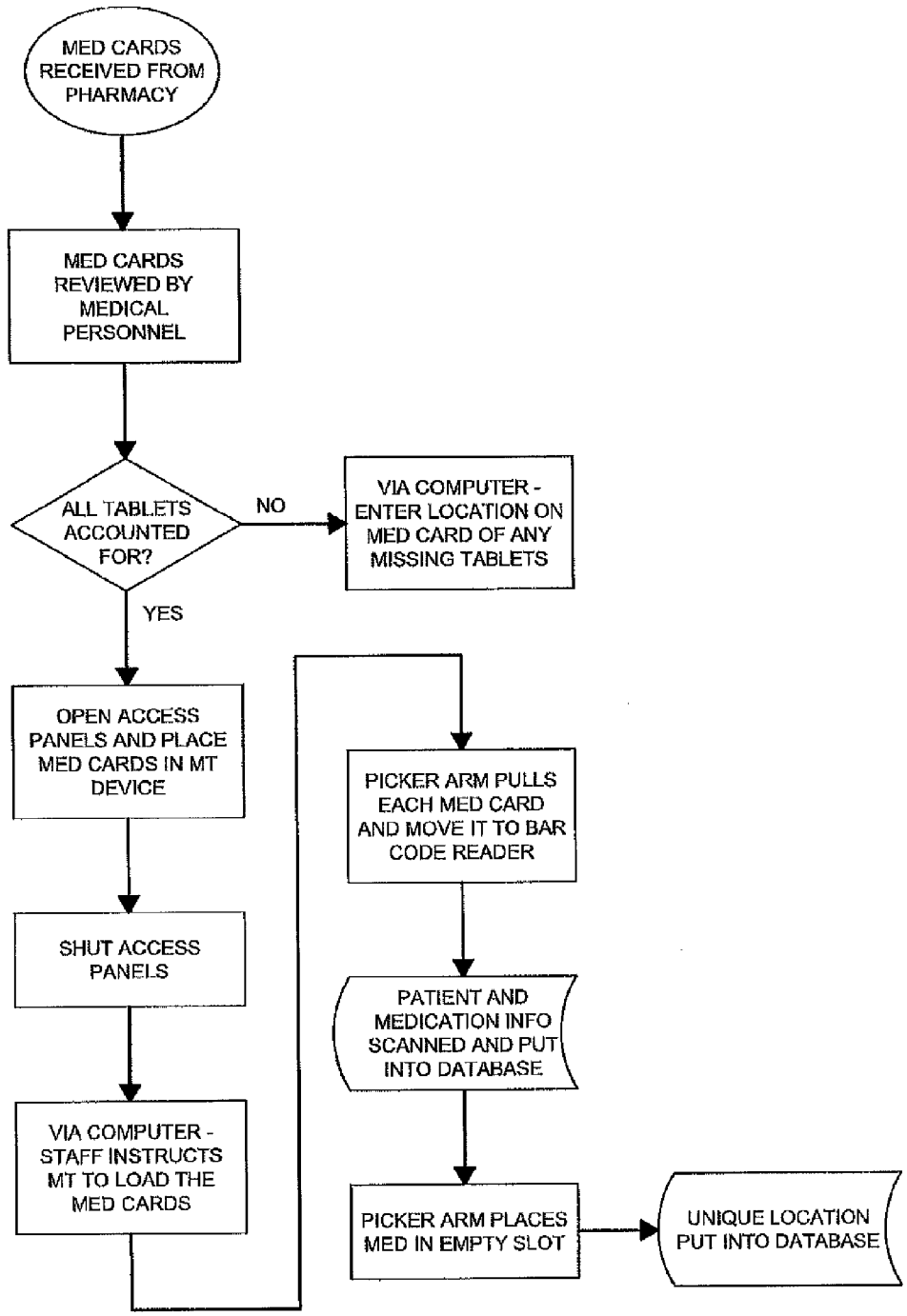
FIG. 17 is a flow chart of the method for loading the automated medication delivery system.
Figure 18:
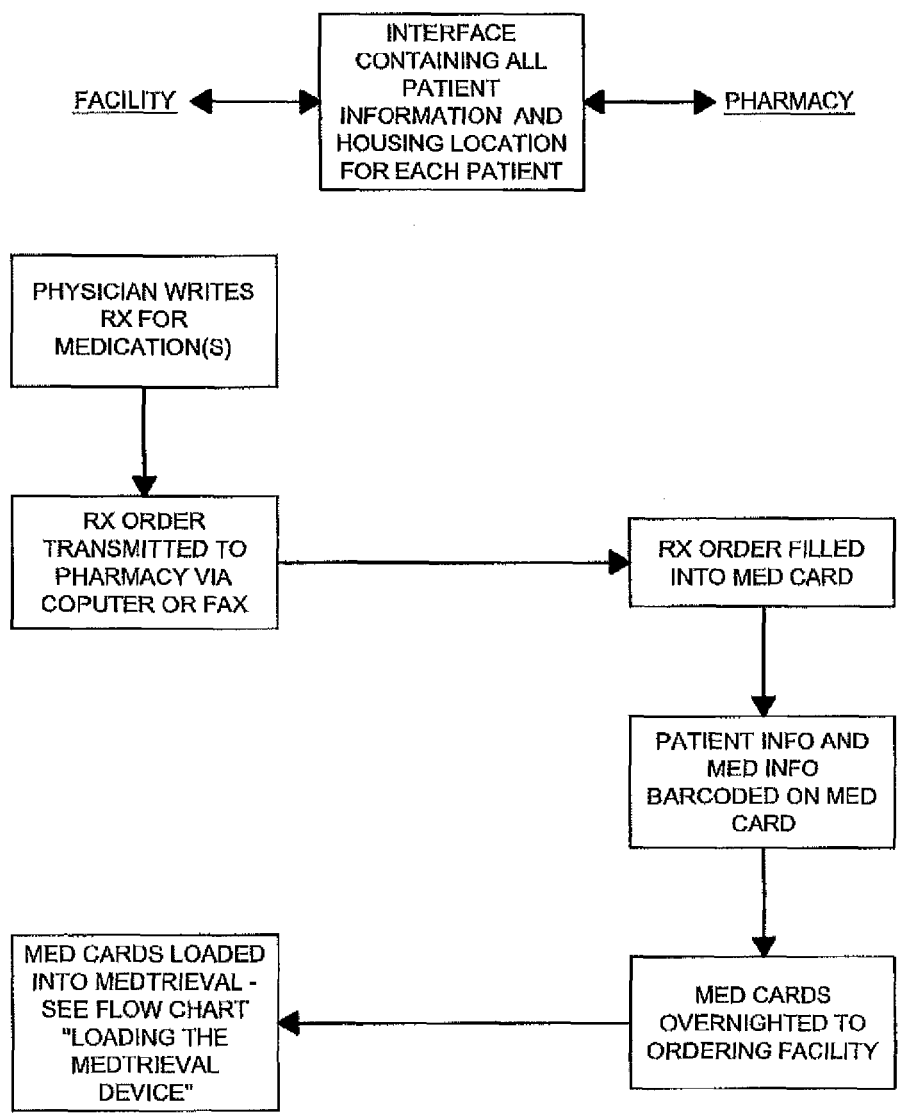
FIG. 18 is a flow chart of the filling of the prescription for the med cards.

The second sub-method highlights the loading process and is shown in FIG. 17. In this sub-method, the medical staff preferably inputs med card 28 into storage facility 12. The group of med cards 28 is received from the pharmacy. Each med card 28 has all of the pertinent patient information already printed upon it, along with barcode 36 that associates the patient information and medication.

The staff member, or members, enters medication room 196 through access door 14 with med cards 28 received from the pharmacy. Each med card 28 is inspected by at least one staff member for completeness, accuracy and any missing medications. All missing medications on med card 28 are identified by individual blisters 118. The information is entered into terminal 194, which is in electronic communication with controller 38 and database 160.

The staff member places the inspected med card 28 onto access panel tray 30. In one embodiment, controller 38 engages barcode scanner 34 to record barcode 36 while med card 28 is upon access panel tray 30. In another embodiment, controller engages barcode scanner 34 after removing med card 28 from access panel tray 30. In an alternative embodiment, the staff member directly places med card 28 into storage bin 24 and engages controller 38, automatically or through terminal 194, to use retrieval device 42 to remove, scan and store it.

Controller 38 next engages retrieval device 42 using retriever 64 to pick up the scanned med card 28. Controller 38 assigns med card 28 to an empty storage bin 24 and moves retrieval device 42 to insert med card 28 therein.

The third sub-method highlights the patient request process. This process is similar to the fourth sub-method shown in FIGS. 16A and 16B. The third sub-method is demonstrated through an example operation of storage facility 12. In the example, the facility is a prison or large institutional hospital.

A patient approaches the first input station 46. Using input port 52 and display device 56, the patient proceeds to login by entering a unique number assigned to them, along with a personal identification number. Positive identification device 54 in this instance is a finger print biometric device. The patient places their finger on positive identification device 54 for verification of their identity. A receipt is printed and dispensed to the patient using printer 158.

Once the patient's identity is verified, a menu of at least one medication associated with that patient is shown on display device 56. The menu indicates all medication available for dispensing at that time. Using first input station 46, the patient makes a request for the medication by selecting the medication desired. If several medications are available, the menu allows the patient to select all dispensable medications.

Upon receipt of the request, controller 38 identifies the specific storage bin 24 containing the patient's med card 28. Controller 38 also identifies that the medication is not a "keep on person" medication and that the medication must be crushed. As known to those skilled in the art, institutions identify certain medications as "keep on person" medications when those medications must remain with the patient. For example, a patient with severe asthma may need to carry their medication with them at all times in the event of an asthma attack.

Controller 38 moves picker arm 62 vertically and laterally to position retriever 64 immediately adjacent to the specific storage bin 24 containing the patient's med card 28. Controller 38 extends picker arm 62 through rotatable collar 70 until retriever 64 clamps med card 28. Controller 38 next retracts picker arm 62 to a neutral position.

Controller 38 moves picker arm 62 vertically and laterally to position retriever 64 adjacent to barcode scanner 34. Controller 38 again extends picker arm 62 through rotatable collar 70 to scan barcode 36 on med card 28. Picker arm 62 is again retracted to a neutral position. Depending upon the particular location of storage bin 24, rotatable collar 70 may have rotated picker arm 62 one or more times to scan barcode 36.

Controller 38 moves picker arm 62 vertically and laterally until med card 28 is aligned with tray 110. Once aligned, controller 38 extends picker arm 62 through rotatable collar 70 to place med card 28 onto tray 110. Since tray 110 is sized to accept med card 110, blisters 118 are aligned with holes 112. Depending upon the particular location of storage bin 24, rotatable collar 70 may have rotated picker arm 62 one or more times to align med card 28 with tray 110. Picker arm 62 may optionally release med card 28. In the preferred embodiment, picker arm 62 retains med card 28 until after punchout system 80 is through with the extraction process of pill 120.

Controller 38 operates punchout system 80 once med card 28 is positioned on tray 110. Controller 38 memory contains the location of all remaining pills 120 in med card 28. Preferably, controller 38 moves punch 108 to a position over blister 118 containing pill 120. Alternatively, picker arm 62 and retriever 64 release med card 28, allowing tray 110 to move and position blister 118 under punch 108. Controller 38 moves punch 108 in a downward direction to push pill 120 through blister 118. Pill 120 falls through hole 112 into catch 114 and out catch opening 116. Since catch 114 is funnel shaped, it does not matter which pill 120 is extracted.

Controller 38 has previously released cup 82 from cup feeder 122 at first conveyor first end 124. Controller 38 positions cup 82 under catch opening 116 by moving cup 82 on first conveyor 84.

Once pill 120 is extracted, controller moves picker arm 62 back to a neutral position on rotatable collar 70. This movement removes med card 28 from tray 110. Preferably, controller 38 moves picker arm 62 to replace med card 28 in the same storage bin 24.

Once pill 120 is in cup 82, controller 38 moves first conveyor 84 to position it under pill crusher 90. Controller 38 moves crusher head 134 in a downward motion until it enters interior 136 of cup 82 and engages pill 120. Pill 120 is crushed by crusher head 134. Anti-contamination film 88 protects crusher head 134. Crusher head is moved upward to a neutral position. Once in the neutral position, controller 38 causes first spool 130 and second spool 132 to rotate and remove the contaminated portion of anti-contamination film 88 from near crusher head 134.

Controller 38 engages first conveyor 84 to move cup 82 to a position in front of first cup dispensing slot 96. Once positioned, controller moves cup sweeper 92 to push cup 82 into first cup dispensing slot 96. Printer 158 produces a receipt and deposits the receipt in or near cup 82 while cup 82 is in first cup dispensing slot 96. The patient is now able to access their medication.

Controller 38 updates database 160 with the details of the transaction to include the specific pill extracted from med card 28.

If the patient is to receive "keep on person" medication, controller 38 directs delivery of med card 28 to second conveyor first end 138. Once med card 28 is on second conveyor 86, controller 38 moves second conveyor 86 until med card 28 is positioned in front of first med card dispensing slot 100. Once there, controller 38 engages med card sweeper 92 to push med card 28 into first med card dispensing slot 100. Printer 158 produces a receipt and deposits the receipt with med card 28 while med card 28 is in first med card dispensing slot 100. The receipt may contain additional information about the medication to include drug interaction warnings and side effects. The patient is now able to access their medication.

Figure 16B:
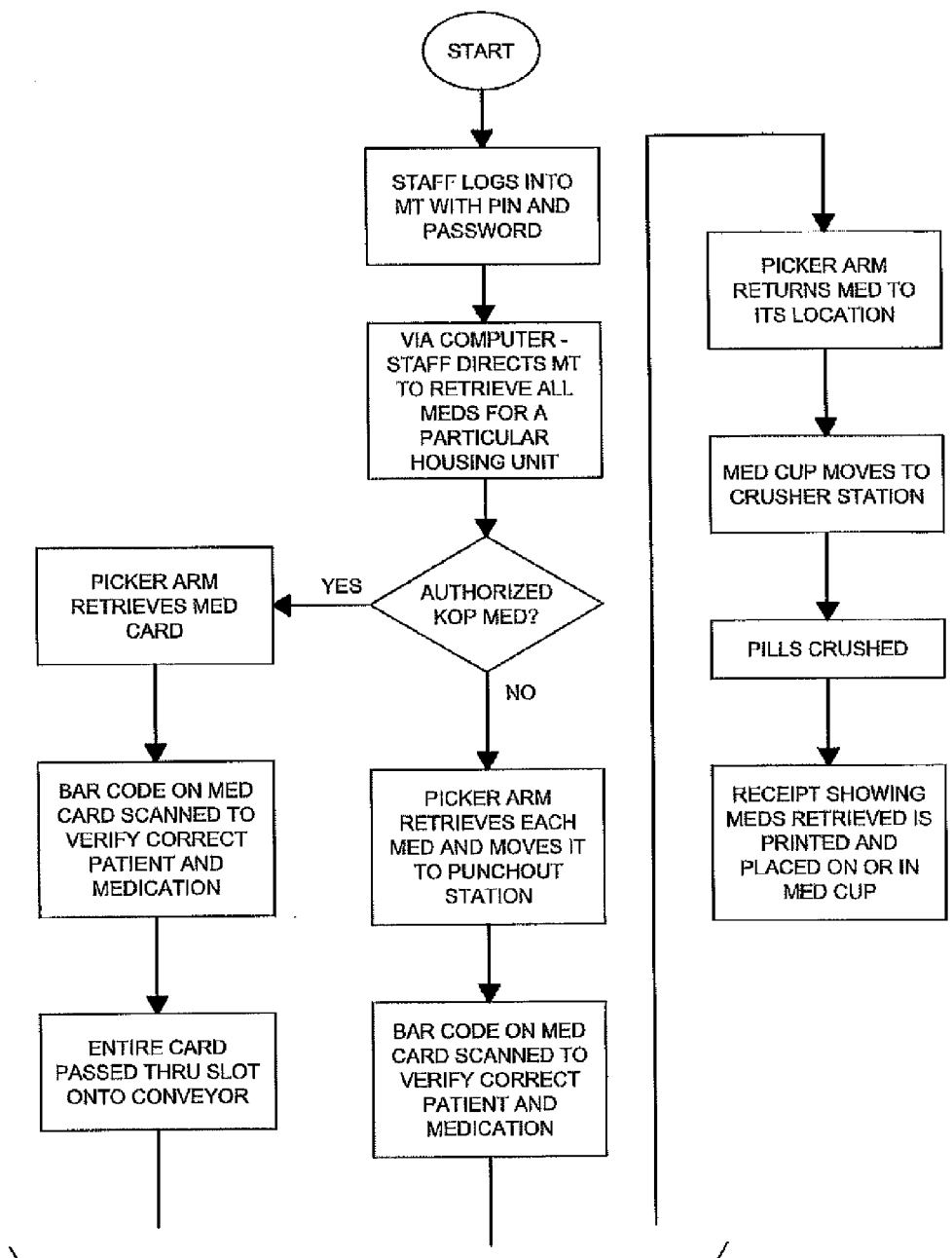

The fourth sub-method is for a staff member to request medication for a group of patients, an entire housing unit or an entire wing. The fourth sub-method is shown in FIGS. 16A and 16B.

In some situations, patients are unable to come to a central medication distribution site. Thus, facility staff member may need to retrieve all of the medication for a particular room, housing unit, or wing. In that situation, the staff member approaches a second input station (not shown) and logins using a second input port (not shown), a second display device (not shown), and a second positive identification device (not shown). Second input station is preferably positioned in near inner side wall 16 or first end wall 126. Second input station is also in electronic communication with controller 38.

After the staff member enters their unique identifying number and personal identification number, they may be required to further provide positive identification by a finger print scanner, retinal scanner, or voice identification device. Once the staff member's identity is verified by controller 38, they will have a different set of menu options presented to them. Preferably, the staff member is able to select an individual patient, a group of patients, an entire housing unit or wing, and/or a combination thereof. From that grouping, the staff member selects the medication to be dispensed at that time. Controller 38 has the medical records of the patients on file and is able to determine which medication must be dispensed.

Controller 38 repeats most of the process used for the individual patient identified in the third sub-method, but it does not use cup sweeper 92 or med card sweeper 94. Instead, controller 38 uses first conveyor 84 to deliver all of the medication in cups 82 through second cup dispensing slot 98. Printer 158 prints the patient information for each cup 82. At that point, controller 38 moves cups 82 on distribution conveyor 104. The staff member removes cups 82 from distribution conveyor 104. A safety check device 190 provides feedback to controller 38 to prevent cups 82 from falling off of distribution conveyor 104.

Additionally, controller 38 uses second conveyor 86 to deliver all med cards 28 that are "keep on person" medications to second med card dispensing slot 102. The med cards 28 are delivered to catch basket 192. The staff member removes all med cards 28 from catch basket 192.

The fourth sub-method highlights the staff request process. The method includes the following steps shown in FIGS. 16A and 16B:

a. The staff member logs into the second input port with appropriate identifier;
b. the staff member selects the option to retrieve all medication for a particular patient, group of patients, housing unit or wing;
c. controller 38 identifies if any of the medication is "keep on person" (KOP) medication
d. if any of the medication is a KOP medication, controller 38 directs retrieval device 42 to use picker arm 62 and retriever 64 to retrieve med card 28:
  i. barcode 36 on med card 28 is scanned and verified that medication is correct for patient;
  ii. the entire med card 28 is passed through second med card dispensing slot 102 to catch basket 192;
  iii. database 160 is electronically updated;
e. If none of medication is a KOP, controller 38 directs retrieval device 42 using picker arm 62 and retriever 64 to retrieve med card 28:
  i. retrieval device 42 using picker arm 62 moves med card 28 to punchout system 80;
  ii. barcode 36 on med card 28 is scanned to verify the correct medication is being dispensed for the correct patient;
  iii. med card 28 is positioned to allow the next individual pill 120 to be punched out, extracted, from blister 118 on med card 28;
  iv. individual pill 120 is punched out and falls into cup 82;
  v. database 160, medication administration records, are electronically updated;
  vi. database 160 information on med card 28 is updated to determine where next punchout should occur on med card 28;
  vii. controller 38 directs retrieval device 42 using picker arm 62 to return med card 28 to its storage bin 24;
  viii. cup 82 is moved on first conveyor to pill crusher 90 station;
  ix. controller 38 identifies if pill 120 is to be crushed; if so, pill(s) 120 are crushed using crusher head 134; otherwise cup 82 is further conveyed to second cup dispersing slot 98; and
  x. printer 158 prints a receipt showing the medication retrieved; the receipt is placed on or in cup 82.

Figure 15:
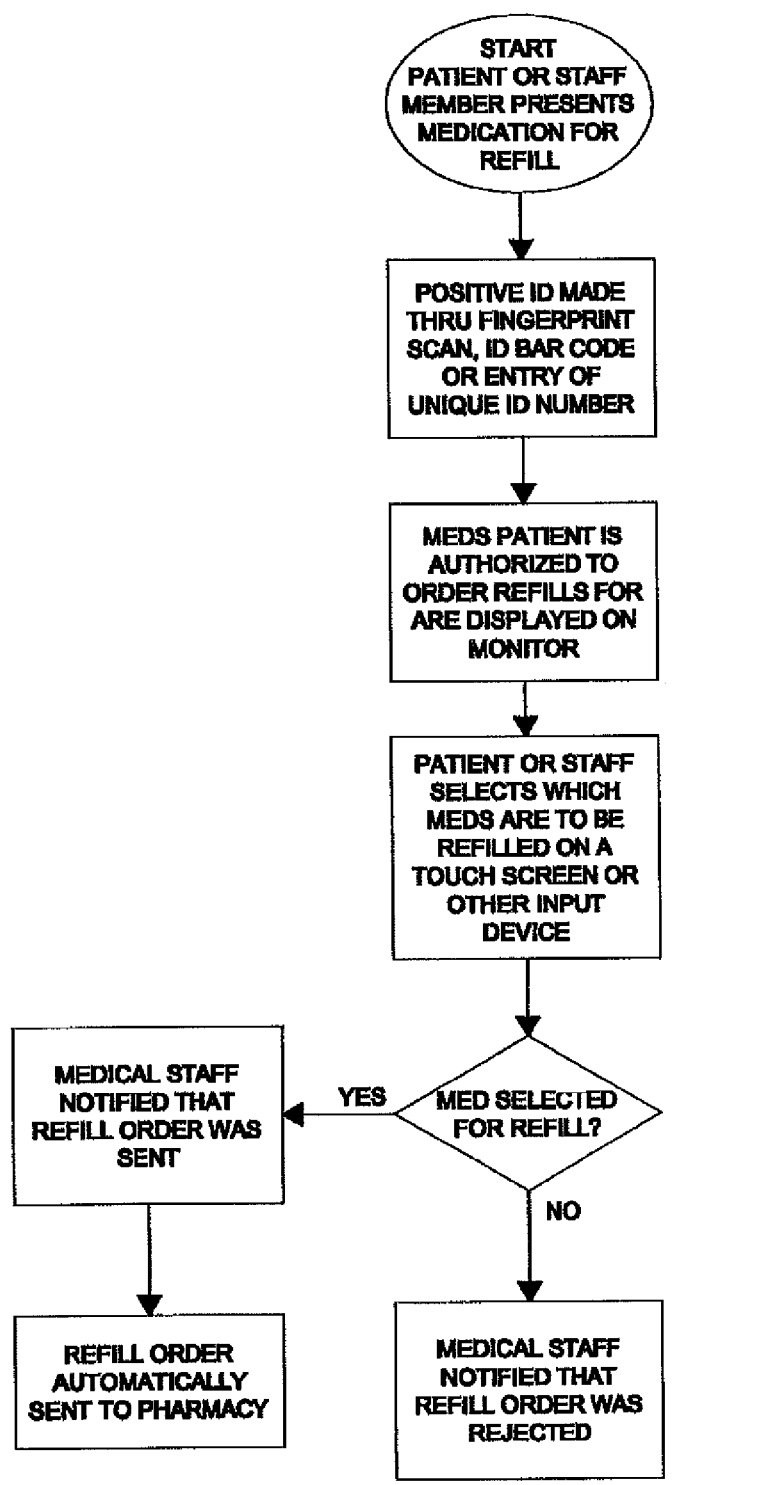
FIG. 15 is flow chart of a patient refill request method.

The fifth sub-method relates to a patient's refill request of medication or a staff member's request for a refill of a medication for a patient. This sub-method is shown in FIG. 15. Controller 38 will display all medications needing refills as part of the original display. If the patient or staff member is only requesting a refill, they may go through the same login process and select that particular option. The fifth sub-method is further outlined in the following steps:

a. The patient or staff member logs into first input station using their unique identifying number, personal identification number, and presenting a positive identification;
b. the positive identification is made through fingerprint scan, retinal scan, or voice identification;
c. the medication(s) the patient is authorized to refill is shown on display device 56;
d. the patient or staff member identifies any or all medications to be refilled;
e. if the medication is selected for refill, the refill order is automatically sent to the pharmacy and the medical staff is notified that a refill order was transmitted; and
f. if the refill order was rejected by the patient or staff member, the medical staff notified that refill order was rejected.

The sixth sub-method relates to the mobility of automated medication delivery system 10. As shown below, cart 50 is used to deliver medication within a facility. Cart 50 may be pushed by a staff member. Alternatively, cart 50 may be semi-autonomous and move through the facility with a staff member. In still another alternative, cart 50 operates autonomously without a staff member. In all situations, cart 50 is in wireless electronic communication with controller 38 and facility staff.

Cart 50 is loaded with med cards 28 by an authorized staff member. In a secure environment, a staff member opens secure access panels 164 to have access to storage bins 24. The staff member uses a remote barcode scanner (not shown) to scan barcode 36 and record the information in on-board computer 170 and controller 38. The remote barcode scanner is mounted within cart 50, and is in electronic communication with on-board computer 170 and controller 38.

The staff member places med card 28 inside of cart 50 under remote barcode scanner. Remote barcode scanner triggers remote retrieval device 174 to collect med card 28. Remote retrieval device 174 selects an empty storage bin 24 and moves med card 28 to that storage bin 24. On-board computer 170 is performing local control of remote barcode scanner and remote retrieval device 174. The particular med card 28 information and storage bin 24 information are locally stored and transmitted to controller 38. The med card 28 information is compared with database 160 by controller 38. Any anomalies are identified to the on-board computer 170, which has remote retrieval device 174 remove med card 28. Once all anomalies are resolved, the med card 28 having trouble is reloaded. After all med cards 28 are loaded, secure access panels 164 are secured.

Once cart 50 is loaded, on-board computer 170 directs it to deliver the medication. Preferably, cart 50 delivers medication to a single room or patient. However, cart 50 can be programmed to deliver medication to a location with several patients.

When the patient accesses cart 50, they use remote input station 172 to login. Using input port 52 and display device 56, the patient proceeds to login by entering a unique number assigned to them, along with a personal identification number. Preferably, the patient further verifies their identity using positive identification device 54. Positive identification device 54 is preferably a biometric device, as described above.

Since, the need for cart 50 implies a higher security area to be serviced, on-board computer 170 records the entire transaction using video camera 144 mounted near remote input station 172. Additionally, the date, time and all other pertinent information is recorded. The recording is wirelessly transmitted to controller 38.

Once the patient's identity is verified, a menu of at least one medication associated with that patient is shown on display device 56. The menu indicates all medication available for dispensing at that time. Using remote input station 172, the patient makes a request for the medication by selecting the medication desired. If several medications are available, the menu allows the patient to select all dispensable medications.

Upon receipt of the request, on-board computer 170 identifies the specific storage bin 24 containing the patient's med card 28. On-board computer 170 also identifies if the medication is a "keep on person" medication, an individual dosage, and if that individual dosage should be crushed.

Within cart 50, on-board computer 170 engages remote retrieval device 174. Picker arm 62 is moved vertically and laterally to position retriever 64 immediately adjacent to the specific storage bin 24 containing the patient's med card 28. On-board computer 170 extends picker arm 62 through rotatable collar 70 until retriever 64 retrieves med card 28. On-board computer 170 next retracts picker arm 62 to a neutral position.

On-board computer 170 next moves picker arm 62 vertically and laterally to position retriever 64 adjacent to barcode scanner 34. On-board computer 170 again extends picker arm 62 through rotatable collar 70 to scan barcode 36 on med card 28. Picker arm 62 is again retracted to a neutral position. Depending upon the particular location of storage bin 24, rotatable collar 70 may have rotated picker arm 62 one or more times to scan barcode 36.

Once med card 28 is scanned, on-board computer 170 moves picker arm 62 vertically and laterally until med card 28 is aligned with tray 110. Once aligned, on-board computer 170 extends picker arm 62 through rotatable collar 70 to place med card 28 onto tray 110. Since tray 110 is sized to accept med card 110, blisters 118 are aligned with holes 112. Depending upon the particular location of storage bin 24, rotatable collar 70 may have rotated picker arm 62 one or more times to align med card 28 with tray 110. Picker arm 62 may optionally release med card 28. In the preferred embodiment, picker arm 62 retains med card 28 until after punchout system 80 is through with the extraction process of pill 120.

On-board computer 170 operates punchout system 80 once med card 28 is positioned on tray 110. On-board computer 170 memory contains the location of all remaining pills 120 in med card 28. Preferably, on-board computer 170 moves punch 108 to a position over blister 118 containing pill 120, Alternatively, picker arm 62 and retriever 64 release med card 28, allowing tray 110 to move and position blister 118 under punch 108. On-board computer 170 moves punch 108 in a downward direction to push pill 120 through blister 118. Pill 120 falls through hole 112 into catch 114 and out catch opening 116. Since catch 114 is funnel shaped, it does not matter which pill 120 is extracted, If an alternative embodiment utilizing pill crusher 90 is used, cup 82 is internally positioned. In this alternative embodiment, on-board computer 170 has previously released cup 82 from cup feeder 122 at cart conveyor first end 186. On-board computer 170 positions cup 82 under catch opening 116 by moving cup 82 on cart conveyor 184.

Once pill 120 is extracted, controller moves picker arm 62 back to a neutral position on rotatable collar 70. This movement removes med card 28 from tray 110. Preferably, on-board computer 170 moves picker arm 62 to replace med card 28 in the same storage bin 24.

Once pill 120 is in cup 82, on-board computer 170 moves first conveyor 84 to position it under pill crusher 90. If pill 120 is to be crushed, on-board computer 170 moves crusher head 134 in a downward motion until it enters interior 136 of cup 82 and engages pill 120. Pill 120 is crushed by crusher head 134. Anti-contamination film 88 protects crusher head 134. Crusher head is moved upward to a neutral position. Once in the neutral position, on-board computer 170 causes first spool 130 and second spool 132 to rotate and remove the contaminated portion of anti-contamination film 88 from near crusher head 134.

If pill 120 is not be crushed, or after being crushed, on-board computer 170 engages first conveyor 84 to move cup 82 to a position in front of remote cup dispensing slot 180. Once positioned, printer 158 produces a receipt and deposits the receipt in or near cup 82 while cup 82 is in remote cup dispensing slot 180. The patient is now able to access their medication.

If the alternative embodiment is not used having pill crusher 90 receiving cup 82 from cup feeder 122, cart conveyor 184 receives pill 120 and positions it in front of remote cup dispensing slot 180.

In yet another embodiment, using pill crusher 90 and not cup feeder 122, the patient selects cup 82 from external cup feeder 198, removes pill 120 from cart conveyor 184, inserts pill 120 into cup 82 and places cup 82 under pill crusher 90. On-board computer 170 knows to detect if cup 82 is positioned under crusher 90 through a detector (not shown). Once cup 82 is in position, pill crusher 90 engages and crushes pill 120. After the crushing event, the patient removes cup 82 with pill 120 in it.

On-board computer 170 updates database 160 via controller 38 with the details of the transaction to include the specific pill extracted from med card 28.

If the patient was to receive "keep on person" medication, controller would have delivered med card 28 to cart shelf 188. Remote retrieval device 174 pushes med card 28 out remote med card dispensing slot 182 a sufficient distance so that the patient may grab med card 28. Printer 158 produces a receipt for the patient. The receipt may contain additional information about the medication to include drug interaction warnings and side effects. The patient is now able to access their medication.

An automated update of the entire transaction is recorded by on-board computer 170 and transmitted to database 160 via controller 38.

Therefore, it will be seen that the apparatus and method of the present invention are well adapted to carry out the ends and advantages mentioned, as well as those inherent therein. While a presently preferred embodiment of the apparatus and method have been described for the purposes of this disclosure, numerous changes in the arrangement and construction of parts in the apparatus, and steps in the method, may be made and executed by those skilled in the art. All such changes are encompassed within the scope and spirit of the appended claims.

What is claimed is:

1. An automated medication delivery system comprising:
 a storage facility having a plurality of storage bins;
 at least one med card carrying a plurality of medications positioned within at least one storage bin;
 a controller in electronic communication with a computer;
 at least one input station associated with said storage facility and in electronic communication with said controller, said input station including:
  an input port;
  a positive identification device;
  a display device;
 a med card retrieval device positioned inside of said storage facility;
 a punchout system adapted to receive said med card from said retrieval device, said punchout system including:
  a punch;
  a tray sized to hold said med card, said tray having a plurality of holes, wherein when said med card is positioned on said tray said plurality of medications carried by said med card align with said plurality of holes in said tray;

a conveyor located inside of said storage facility a cup carried by said conveyor, said cup positioned below at least one hole of said tray;

said storage facility including a cup slot adapted to dispense said cup; and said storage facility including a med card slot adapted to dispense said med card.

2. The automated medication delivery system of claim 1, further comprising a pill crusher.

3. The automated medication delivery system of claim 1, wherein said storage bins are positioned in at least two rows within said storage facility.

4. The automated medication delivery system of claim 3, wherein said retriever is positioned between said rows, said retriever further including:
 a track positioned above said rows of said storage bins, said track extending along at least at length of said rows;
 an elevation rod movably positioned in said track;
 a picker arm movably positioned on said elevation rod; and
 a retriever attached to said picker arm.

5. The automated medication delivery system of claim 4, wherein said retriever is a clamp.

6. The automated medication delivery system of claim 1, wherein said retriever is a spatula.

7. The automated medication delivery system of claim 1, further comprising a second cup slot and a second med card slot.

8. The automated medication delivery system of claim 7, wherein said conveyor is adapted to move said cup through said second cup slot.

9. The automated medication delivery system of claim 7, further comprising a second conveyor, said second conveyor adapted to move said med card from said second conveyor to said second med card slot.

10. The automated medication delivery system of claim 9, further comprising a med card sweeper, wherein said med card sweeper is positioned to push said med card from said second conveyor through said med card slot.

11. The automated medication delivery system of claim 7, further comprising a distribution conveyor, said distribution conveyor positioned to receive said cups from said second cup slot.

12. The automated medication delivery system of claim 1, further comprising a second input port positioned on a second side of said storage facility.

13. The automated medication delivery system of claim 1, wherein said positive identification device includes a biometric identification device.

14. The automated medication delivery system of claim 1, further comprising a barcode scanner positioned within said storage facility at a location suitable for scanning said med cards before and after insertion into said storage bins.

15. The automated medication delivery system of claim 1, further comprising a cup sweeper, wherein said cup sweeper is positioned to push said cup from said conveyor through said cup slot.

16. An automated medication delivery system comprising:
 a storage facility, said storage facility including:
  a secure interior;
  a plurality of storage bins positioned within said secure interior, said storage bins sized to store a med card;
 a controller in electronic communication with a computer, said controller being attached to said storage facility and adapted to control said facility, wherein said controller stores information associated with each of said med cards;
 at least one barcode scanner positioned within said facility and capable of scanning said med cards before insertion into said storage bins and after removal from said storage bins; said barcode scanner in electronic communication with said controller;
 at least one input station incorporated with said storage facility and in electronic communication with said controller, said input station including:
  an input port positioned on a side of said storage facility for entering a user's personal identification data;
  a positive identification device;
  a display device;
  a menu displaying at least one medication associated with a patient, said medication available for dispensing, said menu presented on said display device;
 a retrieval device in electronic communication with said controller and positioned within said facility, said retrieval device including:
  a track;
  an elevation rod movably mounted in said track;
  a picker arm movably mounted on said elevation rod;
  a retriever attached to said picker arm;
 a dispensing device positioned within said facility, said dispensing device including:
  a punchout system positioned inside of said facility and in electronic communication with said controller, said punchout system adapted to receive said med card from said retrieval device, said punchout system including:
   a punch;
   a tray sized to hold said med card, said tray having a plurality of holes thereon, wherein said holes are compatible with a plurality of pills positioned on said med card;
  a cup positioned below said holes, said cup sized to receive one of said plurality of pills;
  a first conveyor having said cup positioned thereon;
  a second conveyor being positioned to receive said med card;
  an anti-contamination film mounted on and stretched between a first and a second spool;
  a pill crusher having a crusher head and positioned between said first and second spools, wherein said anti-contamination film is positioned between said crusher head and an interior of said cup;
  a cup sweeper positioned to move said cup from said first conveyor;
  a med card sweeper positioned to move said med card from said second conveyor;
  at least one cup dispensing slot, said cup dispensing slot being positioned to receive said cup from said cup sweeper;
  at least one med card dispensing slot, said med card dispensing slot positioned to receive said med card from said med card sweeper;
 a positive consumption feedback device in electronic communication with said controller; and
 an audio/video communications link with a separate location, said audio/video communications link providing real-time positive consumption feedback to said separate location.

17. The automated medication delivery system of claim 16, wherein said retriever is a clamp.

18. The automated medication delivery system of claim 16, wherein said retriever is a spatula.

19. The automated medication delivery system of claim 16, wherein said positive identification device is a biometric device selected from the group consisting of a finger print identification device, a retinal scan identification device, and a voice identification device.

20. The automated medication delivery system of claim 16, further comprising a drinking water dispenser.

21. The automated medication delivery system of claim 16, further comprising a staff member input station including:
   a second input port adapted to allow entry of at least one personal identifying data element associated with said staff member; and
   a second positive identification device.

22. The automated medication delivery system of claim 21, further comprising a second cup dispensing slot positioned to allow access to only said staff member.

23. The automated medication delivery system of claim 21, further comprising a second med card dispensing slot positioned to allow access to only said staff member.

24. The automated medication delivery system of claim 21, further comprising a distribution conveyor proximately positioned to receive said cups from said first conveyor.

25. The automated medication delivery system of claim 16 further comprising a mobile delivery system associated with said automated medication delivery system, said mobile delivery system comprising:
   a cart;
   said storage bins internally positioned within said cart;
   an on-board computer in wireless electronic communication with said controller, wherein said on-board computer is attached to said cart provides local control of said cart;
   a wireless communications device providing electronic communication for said on-board computer;
   at least one remote input station incorporated with said cart and in electronic communication with said on-board computer, said input station including:
      an input port positioned on a side of said cart for entering a user's personal identification data;
      a positive identification device;
      a display device;
      a menu displaying at least one medication associated with a patient, said medication available for dispensing, said menu presented on said display device;
   a remote retrieval device positioned inside of said cart capable of retrieving said med cards from said storage bins;
   said punchout system positioned inside of said cart and adapted to receive said med card from said retrieval device, said punchout system including:
      a punch;
      a tray sized to hold said med card, said tray having a plurality of holes thereon, wherein said holes are compatible with a plurality of pills positioned on said med card;
   a cup slot positioned in said side of said cart, said cup slot adapted to dispense said cup;
   a med card slot positioned in said side of said cart, said med card slot adapted to dispense said med card.

26. The mobile automated medication delivery system of claim 25, wherein said cart is robotic.

27. The mobile automated medication delivery system of claim 25, further comprising a pill crusher positioned inside of said storage facility between said punchout system and said cup slot, said pill crusher having an anti-contamination film positioned between a crusher head and an interior of said cup.

28. The mobile automated medication delivery system of claim 25, wherein said retriever is positioned adjacent to said storage bins, said retriever further including:
   a track positioned above said storage bins, said track extending along at least a length of said storage bins;
   an elevation rod movably positioned in said track;
   a picker arm movably positioned on said elevation rod; and
   a retriever attached to said picker arm.

29. The mobile automated medication delivery system of claim 25, wherein said retriever is a clamp.

30. The mobile automated medication delivery system of claim 25, wherein said retriever is a spatula.

31. The mobile automated medication delivery system of claim 25, wherein said positive identification device includes a biometric identification device.

32. The mobile automated medication delivery system of claim 25, wherein said cart has at least one secure access panel.

33. The mobile automated medication delivery system of claim 25, further comprising a barcode scanner positioned within said cart, and capable of scanning said med cards before and after insertion into said storage bins.

34. A method for dispensing medication comprising:
   a requestor logging on to an automated medication delivery system by;
   identifying said requestor through a security protocol, said security protocol including:
      said requestor entering a unique identifier associated with said requestor;
      said requestor entering a security password/personal identification number;
      comparing said entries by said requestor with a database in a controller electronically connected to and communicating with said automated medication delivery system;
   displaying at least one medication available for a patient from a list of available medications for said patient, said list of available medications stored in a patient database;
   selecting at least one medication from said list;
   directing said controller to retrieve said medication from a storage bin located in said automated medication delivery system;
   scanning said selected medication with a barcode reader;
   verifying said scanned medication matches said selected medication;
   dispensing said medication according to a pre-selected protocol that identifies said medication as a keep on person medication or an individual dosage medication;
   printing a receipt for said patient, said receipt having information regarding said medication; and
   updating said patient database.

35. The method of claim 34, wherein said dispensing by said pre-selected protocol further comprises:
   identifying all medications in a med card designated as being a keep on person medication;
   delivering said med card designated as keep on person medications to a slot in said automated medication delivery system;
   passing said med card to said requestor through said slot; and,
   repeating until all med cards requested are dispensed.

36. The method of claim 34, wherein said dispensing by said pre-selected protocol further comprises:
   identifying all medication designated as an individual dose medication;

identifying a location on said med card of a pill to be dispensed next;
delivering said med card to a punchout system, said delivering accomplished by a retrieval device positioned inside of said automated medication delivery system;
positioning said med card on said punchout system where said pill is positioned over a hole in a tray sized to hold said med card;
punching out said pill from said med card using a punch;
receiving said pill in a cup, said cup positioned upon a conveyor;
removing said med card from said punchout system;
returning said med card to said storage bin;
moving said conveyor until said cup is positioned under a pill crusher;
replacing said cup under said punchout system with a new cup;
crushing said pills for those that are prescribed to be crushed;
moving said conveyor until said cup is positioned under a printer;
printing a receipt with said printer;
depositing said receipt into said cup;
moving said conveyor until said cup passes through a slot, thereby dispensing said medication to said requestor; and
repeating until all individual doses requested are dispensed.

37. The method of claim 34, further comprising an additional step of verifying said identity of said patient with a biometric device.

* * * * *